United States Patent [19]

Belliotti et al.

[11] Patent Number: 5,208,251

[45] Date of Patent: May 4, 1993

[54] STYRYL PYRAZOLES, ISOXAZOLES AND ANALOGS THEREOF HAVING ACTIVITY AS 5-LIPOXYGENASE INHIBITORS, PHARMACEUTICAL COMPOSITIONS AND METHODS OF USE THEREFOR

[75] Inventors: Thomas R. Belliotti, Ypsilanti; David T. Connor, Ann Arbor; Daniel L. Flynn, Ann Arbor; Catherine R. Kostlan, Ann Arbor; Donald E. Nies, Ann Arbor, all of Mich.

[73] Assignee: Warner-Lambert Company, Morris Plains, N.J.

[21] Appl. No.: 395,165

[22] Filed: Aug. 16, 1989

Related U.S. Application Data

[63] Continuation of Ser. No. 32,730, Apr. 6, 1987, abandoned, which is a continuation-in-part of Ser. No. 910,692, Sep. 22, 1986, abandoned, which is a continuation-in-part of Ser. No. 861,179, May 9, 1986, abandoned.

[51] Int. Cl.$^5$ .................. A61K 31/42; C07D 261/08
[52] U.S. Cl. .................. 514/372; 514/378; 514/380; 514/403; 514/406; 514/407; 548/206; 548/213; 548/214; 548/240; 548/243; 548/245; 548/247; 548/248; 548/373.1; 548/379.4; 548/377.1; 548/376.1; 548/370.4; 548/374.1; 548/379.1
[58] Field of Search .............. 548/206, 213, 214, 240, 548/243, 245, 247, 248, 356, 373, 375, 378, 379; 514/372, 378, 380, 403, 406, 407

[56] References Cited

U.S. PATENT DOCUMENTS

| | | | |
|---|---|---|---|
| 2,639,990 | 5/1953 | Kendall et al. | 548/379 |
| 2,640,056 | 5/1953 | Kendall et al. | 548/379 |
| 2,721,143 | 10/1955 | Kraft et al. | 548/373 |
| 2,946,765 | 7/1960 | Roos et al. | 548/375 |
| 3,133,080 | 5/1964 | Sarkar et al. | 548/379 |
| 3,239,533 | 3/1966 | Kano et al. | 548/247 |
| 3,410,860 | 11/1968 | Haber et al. | 548/247 |
| 3,464,999 | 9/1969 | LeMieux et al. | 548/206 |
| 3,479,365 | 11/1969 | Naito et al. | 548/206 |
| 3,551,440 | 12/1970 | Naito et al. | 548/214 |
| 3,631,169 | 12/1971 | Minami et al. | 548/240 |
| 3,642,812 | 2/1972 | Southern | 548/247 |
| 3,687,971 | 8/1972 | Shen et al. | 548/247 |
| 3,711,495 | 1/1973 | Kulsa et al. | 548/240 |
| 3,721,681 | 3/1973 | Hutton et al. | 548/214 |

(List continued on next page.)

FOREIGN PATENT DOCUMENTS

| | | |
|---|---|---|
| 0005192 | 4/1979 | European Pat. Off. . |
| 0034754 | 2/1980 | European Pat. Off. ............ 514/378 |
| 0162383 | 5/1985 | European Pat. Off. . |
| 0165782 | 6/1985 | European Pat. Off. . |
| 0165784 | 6/1985 | European Pat. Off. . |
| 1900349 | 8/1970 | Fed. Rep. of Germany ...... 548/379 |
| 138770 | 11/1979 | German Democratic Rep. ............ 548/373 |
| 40468 | 3/1982 | Japan ............ 548/356 |
| 177977 | 10/1983 | Japan ............ 548/373 |
| 1040266 | 2/1986 | Japan ............ 548/378 |
| 717046 | 2/1980 | U.S.S.R. ............ 548/378 |
| 792872 | 9/1981 | U.S.S.R. ............ 548/240 |

OTHER PUBLICATIONS

Howe et al., Chem Abst., 89, 163478p (1978).
Elkasaby et al., Indian J. Chem, 20B, pp. 366-368 (1981).
Nelson et al., J. Org. Chem., 37 (17) pp. 2686-2688 (1972).
Shridhar et al., Indian J. Chem., 20B, pp. 401-403 (1981).

*Primary Examiner*—Marianne M. Cintins
*Assistant Examiner*—Catherine S. Kilby Scalzo
*Attorney, Agent, or Firm*—Joan Thierstein; Ronald A. Daignault

[57] ABSTRACT

The present invention is 3,5-substituted, isoxazoles, pyrazoles, isothiazoles, and analogs thereof having 5-lipoxygenase or cyclooxygenase inhibiting activity or as a sunscreen.

79 Claims, No Drawings

U.S. PATENT DOCUMENTS

| | | | |
|---|---|---|---|
| 3,752,819 | 8/1973 | Philippe | 548/248 |
| 3,772,284 | 11/1973 | Singh et al. | 548/247 |
| 3,835,126 | 9/1974 | Mengler et al. | 548/379 |
| 3,849,436 | 11/1974 | Johnson | 548/373 |
| 3,895,027 | 7/1975 | Katner | 548/378 |
| 3,910,949 | 10/1975 | Stepek et al. | 548/373 |
| 3,948,937 | 4/1976 | Johnson et al. | 548/378 |
| 4,032,644 | 6/1977 | Nadelson | 548/247 |
| 4,042,706 | 8/1977 | Ahrens et al. | 548/378 |
| 4,045,169 | 8/1977 | Mengler | 548/378 |
| 4,095,025 | 6/1978 | Newberry | 548/378 |
| 4,113,957 | 9/1978 | Moller et al. | 548/375 |
| 4,129,568 | 12/1978 | Howe | 548/240 |
| 4,139,366 | 2/1979 | Howe | 548/240 |
| 4,140,515 | 2/1979 | Howe | 548/214 |
| 4,153,707 | 5/1979 | Moon | 548/247 |
| 4,229,204 | 10/1980 | Howe | 548/247 |
| 4,346,094 | 8/1982 | Beck et al. | 548/206 |
| 4,397,853 | 8/1983 | Kawakita et al. | 548/240 |
| 4,451,476 | 5/1984 | Diana | 548/247 |
| 4,495,195 | 1/1985 | Beck et al. | 548/378 |
| 4,500,340 | 2/1985 | Becker et al. | 548/247 |
| 4,564,684 | 1/1986 | Copp et al. | 548/362 |

STYRYL PYRAZOLES, ISOXAZOLES AND ANALOGS THEREOF HAVING ACTIVITY AS 5-LIPOXYGENASE INHIBITORS, PHARMACEUTICAL COMPOSITIONS AND METHODS OF USE THEREFOR

This is a continuation of U.S. Ser. No. 032,730 filed Apr. 6, 1987 now abandoned which is a continuation in part of U.S. Ser. No. 910,692 filed Sep. 22, 1986, abandoned, which is a continuation in part of U.S. Ser. No. 861,179 filed May 9, 1986, abandoned.

BACKGROUND OF THE INVENTION

The present invention is novel styryl pyrazoles and analogs thereof as well as pharmaceutical compositions and methods of use therefor.

Styryl isoxazole derivatives having cardiovascular activity are known. For example, European Patent Applications No. 34754 and NO. 5192 and German Application No. 2943-405 having Derwent Abstract Nos. 66318 D/37, 84501 B/47 and 34567 D/20, respectively, disclose a compound of the general formula

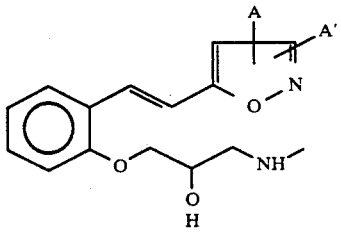

However, the present compounds differ from such references by a completely different side chain from that shown above linked to the phenyl at the 2-position through an ether group in each reference. Further, European Patent Application No. 5186 reviewed by Derwent Abstract No. 844908/47 discloses a intermediate isoxazole of the formula

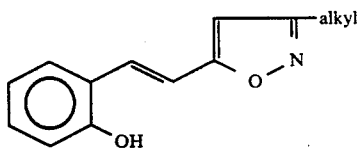

for which no pharmaceutical utility is disclosed.

Pyrazole derivatives having biological, specifically antiinflammatory, activity are found in Belgian Patent Nos. 819,890 and 844,972 abstracted in Derwent Abstract Nos. 20948W/13 and 09405Y/06, respectively. A similar derivative is disclosed in German Patent No. 2920941 of Derwent Abstract No. 86535C/49. However, each of these disclosed pyrazole derivatives requires substituents on adjacent carbons of the pyrazole ring.

Specifically excluded from the compounds of the present invention are the compounds of French Patent No. 2104932 of Derwent Abstract No. 46150T-B useful as hypocholesterolemics, antiinflammatories, analgesics, sedatives, antipyretics, and in some instances diuretics The compounds of the French Patent generally have the formula

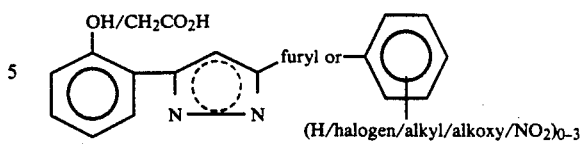

Finally, of lesser interest numerous imidazoles are known having various pharmaceutical activity. For example, U.S. Pat. No. 3,812,111 and British 1,046,248 disclose compounds of general formula

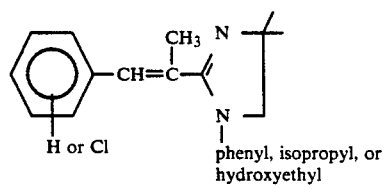

and

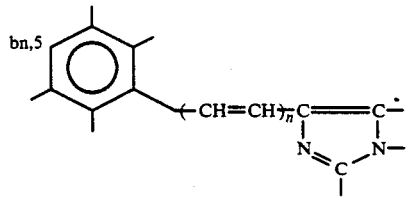

respectively wherein the represents various substituents. However, the imidazoles are compounds differing from the present invention in that the compounds have a different ring system from the pyrazoles.

Thus, the novel compounds that are the present invention provide activity for use in the treatment of diseases in which 5-lipoxygenase enzyme activity contributes to the pathological condition. For example, the use for the present novel compounds, compositions and methods of use is for allergy, asthma, arthritis, skin disorders, such as psoriasis or acne, inflammation, for example, inflammatory bowel disease or pain, and further, also cardiovascular disorders including infarction, angina, arrhythmias, stroke, migraine, atherosclerosis, ulcers and other conditions particularly benefited by cytoprotective activity. An additional property of the present novel compounds now found to provide usefulness, for example, as sun screens, is absorption of ultraviolet light.

SUMMARY OF THE INVENTION

The present invention is a novel compound of the formula (I)

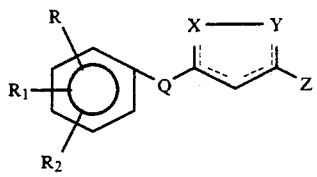

and pharmaceutically acceptable salts thereof; wherein
(1) ===== is a single or double bond;

(2) R, $R_1$, and $R_2$ may be the same or different and are selected from the group consisting of hydrogen, lower alkyl, hydroxy, $OR_3$ wherein $R_3$ is lower alkyl, C(O)$OR_4$ wherein $R_4$ is hydrogen or lower alkyl, $OC(O)R_3$ wherein $R_3$ is independently as defined above, $C(O)R_3$ wherein $R_3$ is independently as defined above, $NR_6R_7$, wherein $R_6$ and $R_7$ may be the same or different and are hydrogen or lower alkyl, $NHC(O)R_3$ wherein $R_3$ is independently as defined above, NHCHO, $NHSO_2R_3$ wherein $R_3$ is independently as defined above, $NHCONHR_4$ wherein $R_4$ is independently as defined above, hydroxymethyl, halogen, trifluoromethyl, $SR_4$ wherein $R_4$ is independently as defined above, or nitro;

(3) Q is $(CH_2)_n$ wherein n is an integer of zero to four, CH=CH or

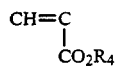

wherein $R_4$ is independently as defined above;

(4) X and Y are (i) N, (ii) $NR_5$ wherein $R_5$ is hydrogen, lower alkyl,

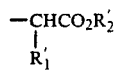

wherein $R'_1$ and $R'_2$ may be the same or different and are hydrogen or lower alkyl, $C(O)R_3$ wherein $R_3$ is independently as defined above, cycloalkyl of from three to twenty carbons having of from three to eight ring carbons, aryl, or aralkyl, (iii) O, or (iv) S; with the proviso that X and Y cannot both be N, $NR_5$, O or S at once and with the proviso that one of X and Y cannot be O at the same time the other of X and Y is S or NR and that one of X and Y cannot be S at the same time the other of X and Y is $NR_5$;

(5) Z is H, lower alkyl, aryl, aralkyl, $OC(O)R_3$ wherein $R_3$ is independently as defined above, C(O)$OR_4$ wherein $R_4$ is independently as defined above, $C(O)R_3$ wherein $R_3$ is independently as defined above, $CH(R'_1)CO_2R'_2$ wherein $R'_1$ and $R'_2$ are independently as defined above, halogen, trifluoromethyl,

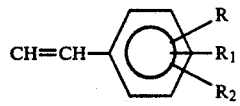

wherein R, $R_1$ and $R_2$ are independently as defined above, heteroaryl, or heteroaralkyl; with the overall proviso that when one of R, $R_1$, and $R_2$ is 2-hydroxy, X is O, Y is N and Q is CH=CH, then Z cannot be H or alkyl; and also with the overall proviso that when R, $R_1$, and $R_2$ are hydroxy or lower alkyl, Y and X are N or NH, and n is zero then Z cannot be furyl or phenyl unsubstituted or substituted with halogen, trifluoromethyl, alkyl, alkoxy or $NO_2$.

The present invention is also a pharmaceutical composition for treating a disease such as allergy, asthma, arthritis, psoriasis, acne, inflammation, pain, or cardiovascular disorders comprising an antiallergic, antiinflammatory, analgesic, or beneficial cardiovascular effective amount of the compound of formula (I)

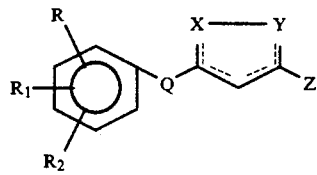

and pharmaceutically acceptable salts thereof; wherein
(1) ===== is a single or double bond;

(2) R, $R_1$, and $R_2$ may be the same or different and are selected from the group consisting of hydrogen, lower alkyl, hydroxy, $OR_3$ wherein $R_3$ is lower alkyl, C(O)$OR_4$ wherein $R_4$ is hydrogen or lower alkyl, $OC(O)R_3$ wherein $R_3$ is independently as defined above, $C(O)R_3$ wherein $R_3$ is independently as defined above $NR_6R_7$ wherein $R_6$ and $R_7$ may be the same or different and are hydrogen or lower alkyl, $NHC(O)R_3$ wherein $R_3$ is independently as defined above, NHCHO, $NHSO_2R_3$ wherein $R_3$ is independently as defined above, $NHCONHR_4$ wherein $R_4$ is independently as defined above, hydroxymethyl, halogen, trifluoromethyl, $SR_4$ wherein $R_4$ is independently as defined above, or nitro;

(3) Q is $(CH_2)_n$ wherein n is an integer of zero to four, CH=CH or

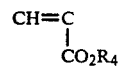

wherein $R_4$ is independently as defined above;

(4) X and Y are (i) N, (ii) $NR_5$ wherein $R_5$ is hydrogen, lower alkyl,

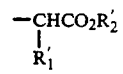

wherein $R'_1$ and $R'_2$ may be the same or different and are hydrogen or lower alkyl, $C(O)R_3$ wherein $R_3$ is independently as defined above, cycloalkyl of from three to twenty carbons having of from three to eight ring carbons, aryl, or aralkyl, (iii) O, (iv) S; with the proviso that X and Y cannot both be N, $NR_5$, O or S at once and with the proviso that one of X and Y cannot be O at the same time the other of X and Y is S or $NR_5$ and that one of X and Y cannot be S at the same time the other of X and Y is $NR_5$;

(5) Z is H, lower alkyl, aryl, aralkyl, $OC(O)R_3$ wherein $R_3$ is independently as defined above, C(O)$OR_4$ wherein $R_4$ is independently as defined above, $C(O)R_3$ wherein $R_3$ is independently as defined above, $CH(R'_1)CO_2R'_2$ wherein $R'_1$ and $R'_2$ are independently as defined above, halogen, trifluoromethyl,

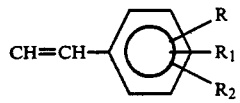

wherein R, R$_1$, and R$_2$ are independently as defined above, heteroaryl, or heteroaralkyl; with the overall proviso that when R, R$_1$, and R$_2$ are hydroxy or lower alkyl, n is zero, Y and X are N or NH, then Z cannot be furyl or phenyl unsubstituted or substituted with halogen, trifluoromethyl, alkyl, alkoxy or NO$_2$ and a pharmaceutically acceptable carrier.

The present invention is also a composition of the compound of formula I not including the overall provisos and a carrier from among the carriers known to be for use in combination with a sunscreen.

Further, the invention is a method for treating mammals having at least one of the diseases noted above by administering an amount effective to treat one of the diseases to such mammals a unit dosage form of the pharmaceutical composition as defined above.

Also, the invention is a method of using a compound of formula I; again as defined above but not including the overall provisos, as a sunscreen, for example, in a coating on humans, in paint and the like.

Finally, the present invention is a process of preparing a compound of formula I as defined above.

DETAILED DESCRIPTION OF THE INVENTION

In the compounds of formula I the term lower alkyl is of one to four carbons, inclusive, and includes methyl, ethyl, propyl, or butyl and isomers thereof.

Halogen includes particularly fluorine, chlorine bromine or iodine.

Aryl is phenyl unsubstituted or substituted by one, two or three substituents of one or more of each of alkyl of one to four carbons, inclusive, OR$_4$ wherein R$_4$ is independently as defined above SR$_4$ wherein R$_4$ is independently as defined above, $$\underset{R_4CO}{\overset{O}{\|}}$$

wherein R$_4$ is independently as defined above, C(O)OR$_4$ wherein R$_4$ is independently as defined above, hydroxymethyl, NR$_6$R$_7$ wherein R$_6$ and R$_7$ are each independently as defined above, or nitro, or halogen.

Aralkyl is an aryl as defined above and attached through an alkylenyl such as methylenyl, ethylenyl, propylenyl, butylenyl and isomers thereof.

Heteroaryl means 2-, or 3-pyrrolyl; 2- or 3-furyl; 2- or 3-thienyl; 2-, 4-, or 5-oxazolyl; 2-, 4-, or 5-thiazolyl; 1-, 2-, or 4-imidazolyl, 2-, 3-, or 4-isothiazolyl, 2-, 3-, or 4-isoxazolyl, 1-, 2-, or 3-pyrazolyl, and 2-, 3-, 4-pyridyl.

The compounds of the present invention contemplate compounds having the following ring systems.

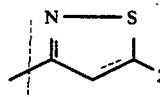 A.

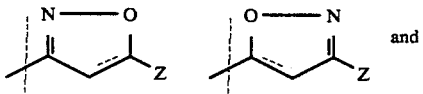 B.

and

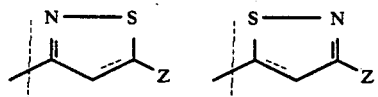 C.

wherein R$_5$ and Z are as defined above.

When R$_5$ is hydrogen it is understood the ring system may be represented by the following equilibrium:

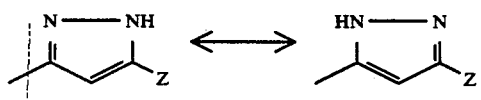

The compounds of formula I are useful both in the free base form, in the form of base salts where possible, and in the form of acid addition salts. The three forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as methanesulfonic acid, benzenesulfonic acid, p-toluenesulfonic acid, and the like, giving the hydrochloride, sulfamate, methanesulfonate, benzenesulfonate, p-toluenesulfonate, and the like, respectively or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are non-toxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di- or trihydroxyalkylamines such as mono-, di- and triethanolamine; amino acids such as arginine, and lysine; quanidine; N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.* 66(1):1–19 (1977).)

The acid addition salts of said basic compounds are prepared either by dissolving the free base of compound I, I' or II in aqueous or aqueous alcohol solution or other suitable solvents containing the appropriate acid or base and isolating the salt by evaporating the solution, or by reacting the free base of compound I, I' or II with an acid as well as reacting compound I, I' or II having an acid group thereon with a base such that the reactions are in an organic solvent, in which case the salt separates directly or can be obtained by concentration of the solution.

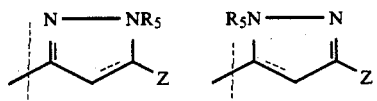

The compounds of the invention may contain an asymmetric carbon atom. Thus, the invention includes the individual stereoisomers, and the mixtures thereof. The individual isomers may be prepared or isolated by methods known in the art.

Compounds of the present invention that are preferred are of formula I wherein Y is N and X is NH or Y is N and X is O.

The most preferred compounds of the present invention are 5-[β-(4'-hydroxy-3',5'-bis(1,1-dimethylethyl)-phenyl)ethenyl]-3-methylisoxazole, 3-[β-(4'-hydroxy-3'-methoxyphenyl)ethenyl]-5-methylpyrazole, and 5-[β-(4'-hydroxy-3',5'-dimethoxy-phenyl)ethenyl]-3-methylisoxazole.

A physician or veterinarian of ordinary skill readily determines a subject who is exhibiting symptoms of any one or more of the diseases described above. Regardless of the route of administration selected, the compounds of the present invention of the formula I as described in pharmaceutical compositions above are formulated into pharmaceutically acceptable dosage forms by conventional methods known to the pharmaceutical art.

The compounds can be administered in such oral unit dosage forms as tablets, capsules, pills, powders, or granules. They also may be administered rectally or vaginally in such forms as suppositories or bougies; they may also be introduced parenterally (e.g. subcutaneously, intravenously, or intramuscularly), using forms known to the pharmaceutical art. They are also introduced directly to an affected area (e.g., in the form of eye drops or by inhalation). For the treatment of asthma or allergies, particularly dermatological disorders; such as erythema, psoriasis and acne, the compounds may also be administered topically in the form of ointments, gels, or the like. However, in general, the preferred route of administration is orally.

An effective but nontoxic quantity of the compound is employed in treatment. The ordinarily skilled physician or veterinarian will readily determine and prescribe the effective amount of the compound to prevent or arrest the progress of the condition for which treatment is administered. In so proceeding, the physician or veterinarian could employ relatively low dosages at first, subsequently increasing the dose until a maximum response is obtained.

Initial dosages of the compounds of formula I of the invention in pharmaceutical compositions are ordinarily in the area of 10 mg up to 2 grams per day orally, preferably 10 mg to 500 mg per dose orally given one to four times daily or as needed. When other forms of administration are employed equivalent doses are administered.

Additionally, the present invention is compositions comprising the compounds of formula I, for use as sunscreens, having a suitable carrier therefor.

The ultraviolet absorbing properties of the compounds of the present invention is generally shown by a comparison with p-aminobenzoic acid which is the active ingredient in most commercial sunscreens. Such properties are within the ultraviolet absorbing ranges of 260 to 300 nM range critical to effectiveness. A representative compound of the invention is compared to p-aminobenzoic acid in the following Table.

TABLE

| Compound | UV max | α |
| --- | --- | --- |
| p-aminobenzoic acid | 285 nM | 132.2 |
| 3-[β-(4'-hydroxy-3'-methoxy- | 292 nM | 111.1 |

TABLE-continued

| Compound | UV max | α |
| --- | --- | --- |
| phenyl)ethenyl]-5-methylpyrazole | | |

The methods of preparation for the compounds of the present invention may, generally, be accomplished in a manner according to the definition of X and Y.

For example, generally compounds of formula I wherein X and Y are each N or NR₅ are prepared in a manner shown by Scheme I as follows:

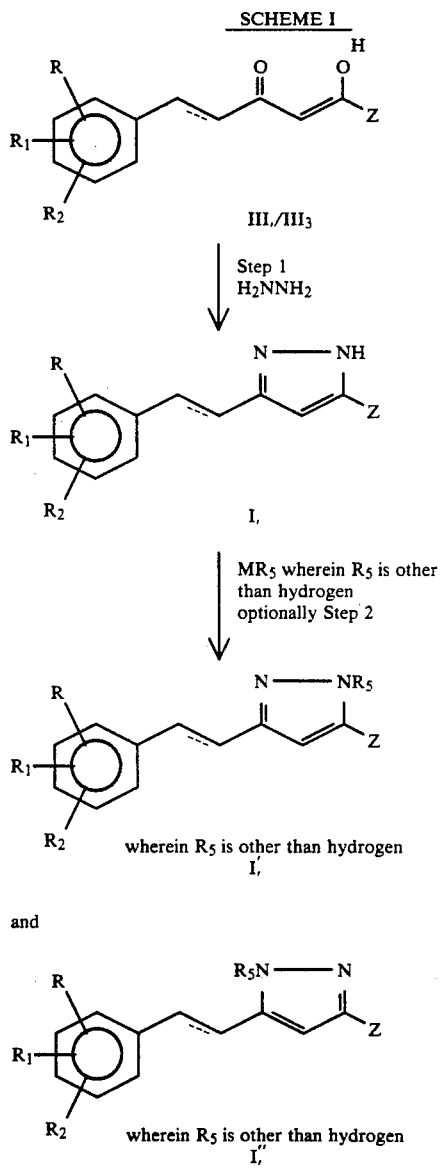

wherein ≈≈≈, R, R₁, R₂, R₅ and Z are as defined above.

In Step 1 of Scheme I equimolar parts of hydrazine hydrate and a compound of the formula III wherein R, R₁, R₂ and Z are as defined above are combined in a solvent such as 1 part ethanol and 1 part butanol, or 2-propanol, and the like. A small amount of about 0.1 ml to 10 ml preferably 0.5 ml of acetic acid is added with the hydrazine hydrate. Optionally, the step 1 product of formula I₁ is further reacted as shown in step II with a compound MR₅ wherein M is an electrofuge such as halogen, sulfonate, or the like and $R_5$ is as defined above but other than hydrogen to obtain a mixture of the compound of formula $I'_1$ and $I''_1$ wherein ====, R, $R_1$, $R_2$, $R_5$ when not hydrogen and Z are as defined above. The compounds $I'_1$ and $I''_1$ may be separated by conventional means.

Similarly compounds of formula I wherein X and Y are each N or $NR_5$ wherein Q is $CH_2$ and n is 1 can be prepared according to the following Scheme Ia using analogous conditions as provided above for Scheme I.

SCHEME Ia

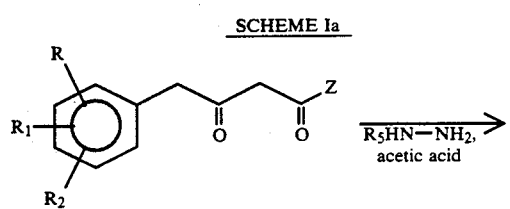

-continued
SCHEME Ia

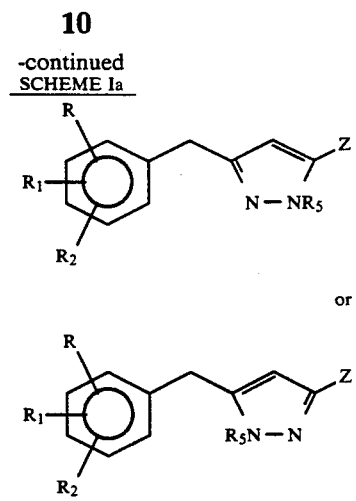

Further, the compound of formula $I'_2$ are prepared as shown in the following Scheme II and IIa.

SCHEME II

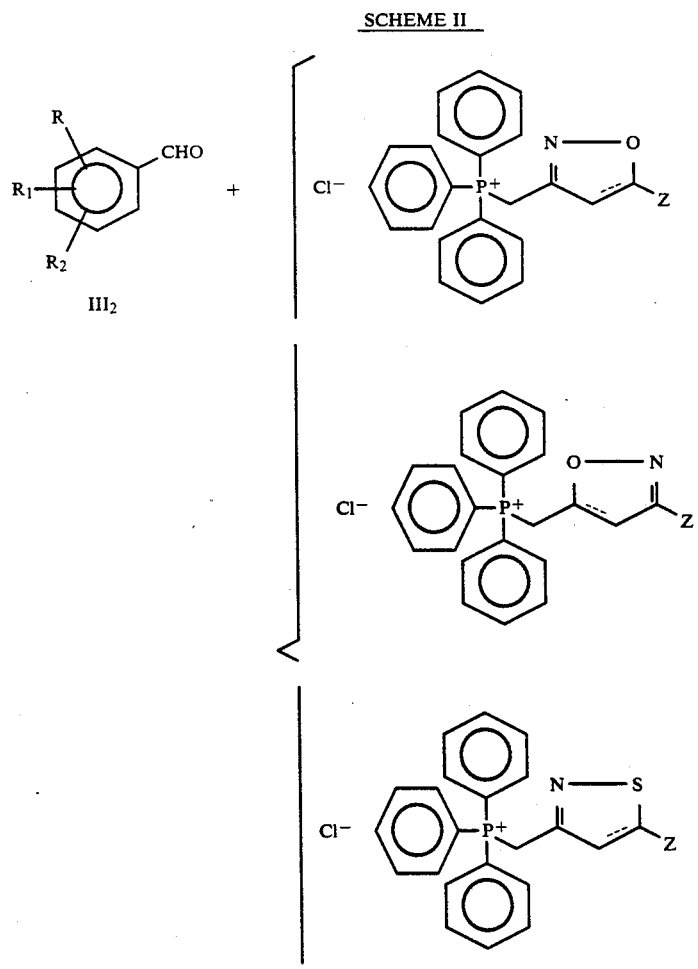

-continued
SCHEME II

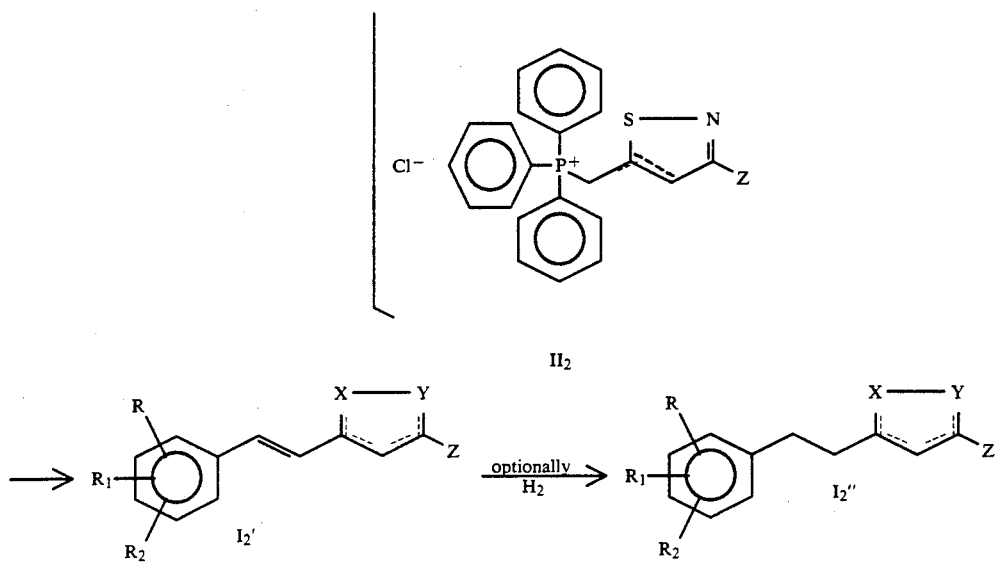

wherein X and Y are O or N and S or N.

wherein R, R$_1$, R$_2$ and Z are as defined above and Y and

SCHEME IIa

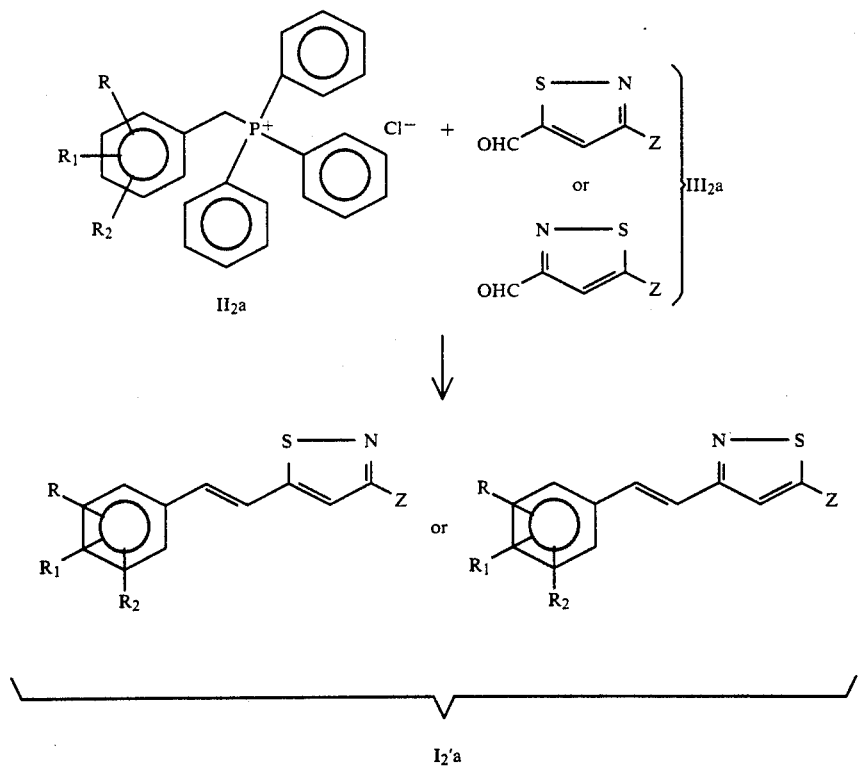

Triphenylphosphonium halide; preferably chloride, of the formula II$_2$ or II$_{2a}$ are contacted by an excess of a compound of the formula III$_2$ or III$_{2a}$ in a solvent such as dimethylsulfoxide, toluene, or the like to which an equivalent amount of potassium t-butoxide is added. The mixture is stirred at about room temperature for from 10 minutes to 2 hours or more under an inert atmosphere. A compound of formula I'$_2$ or I'$_{2a}$ is obtained X are each either N or O and N or S, respectively.

Mild hydrogenation by conventional methods by an ordinarily skilled artisan may be carried out to provide a compound of formula I"$_2$ wherein R, R$_1$, R$_2$ and Z are as defined and Y and X are O or N and S or N, respectively.

Additionally, for compounds wherein Z is defined such that the two substituents on the heterocyclic ring of formula

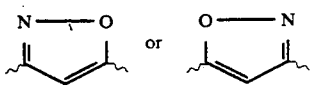

are the same, the compounds may be prepared according to the following scheme III.

SCHEME III

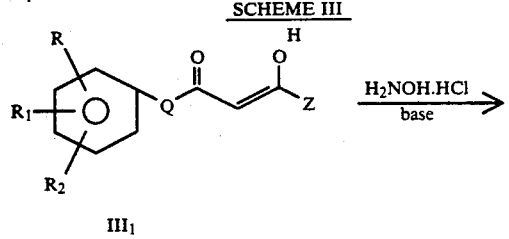

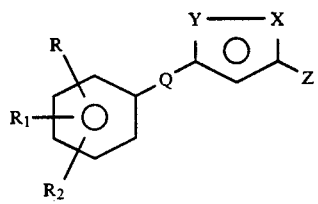

wherein Z is

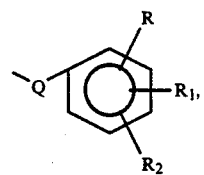

and wherein R, $R_1$, $R_2$, and Q are as defined above and Y and X are either O and M or N and O.

The conditions of the reaction in Scheme III are, generally, carried out with equimolar parts of the compound of formula III and hydroxylamine hydrochloride in a solvent such as methanol, ethanol and the like in the presence of a buffer such as sodium acetate at reflux temperature until completion as determined by TLC.

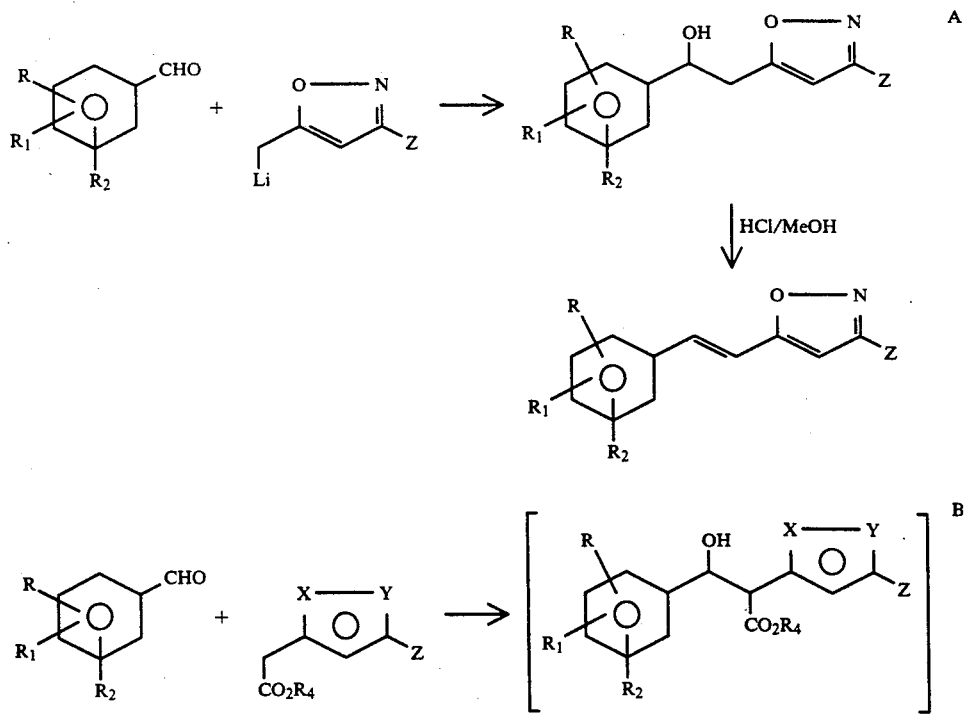

SCHEME IV

-continued

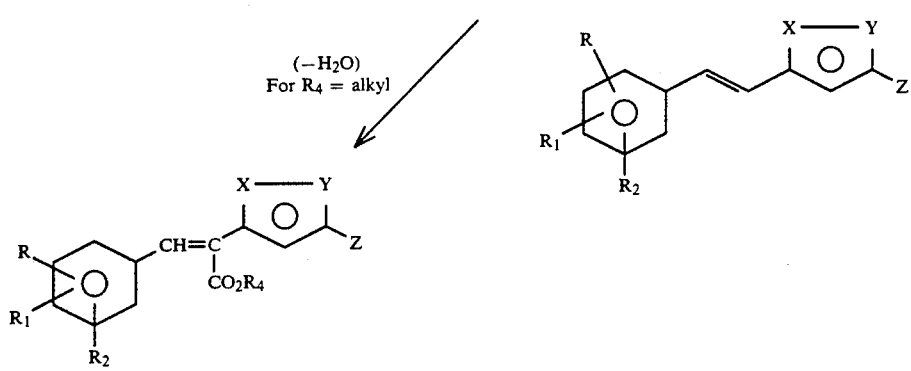

wherein R, $R_1$, $R_2$, and Z are as defined above.

The conditions of the synthesis in Scheme IV step 1 are, generally, carried out in a manner analogous to those described by C. Kashima et al, *Bull. Chem. Soc. Japan*, 46, 310 (1973) and C. Kashima et al, *Heterocycles*, 6, 805 (1977). Unexpectedly the step 2 dehydration when $R_4$ is H or alkyl and also further decarboxylation when $R_4$ is H are carried out in a one pot reaction together with step 1. Conditions for step 2 are analogous to those known in the art and, thus, within the ordinary artisan's skill.

SCHEME V

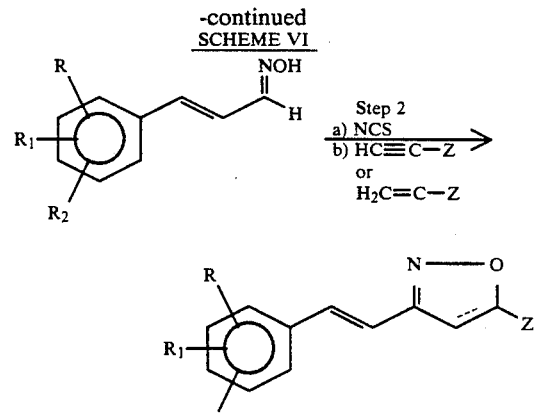

The conditions of the above Scheme V are analogous to those described by M. Nitta, *J. Chem. Soc. Chem. Commun.*, 877, 1982.

Finally, conditions analogous to those described in copending application PD-3493 U.S. Ser. No. 851,003, filed Apr. 11, 1986 are useful in step 1 of Scheme VI below. Step 2 of Scheme VI is carried out using anhydrous conditions in an inert solvent at about the temperature of 0° to 50° C. for from 90 min to 18 hours.

SCHEME VI

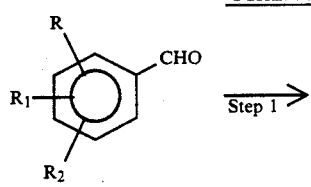

-continued
SCHEME VI

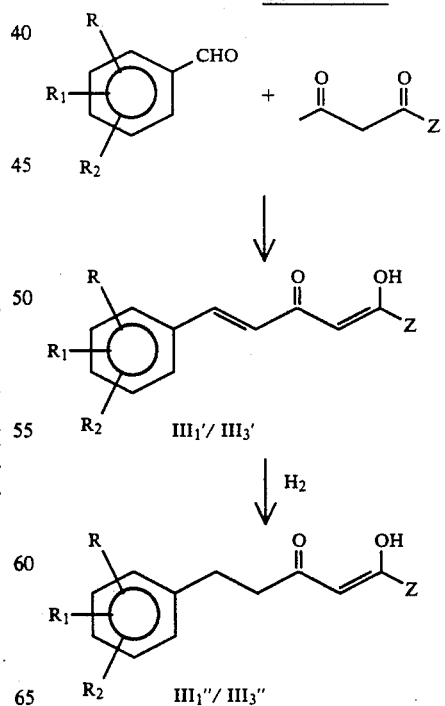

SCHEME VII

The compounds in Scheme VII are compounds wherein R, $R_1$, $R_2$ and Z are as defined above for compounds of formula III'$_3$ and III"$_3$ but III'$_1$ and III"$_1$ are symmetrical.

An alternate preparation for the compounds of formula III$_3$ is as found in Scheme VIII as follows:

SCHEME VIII

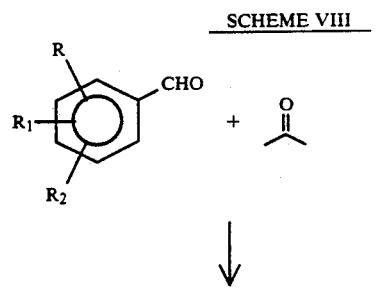

-continued
SCHEME VIII optionally H$_2$

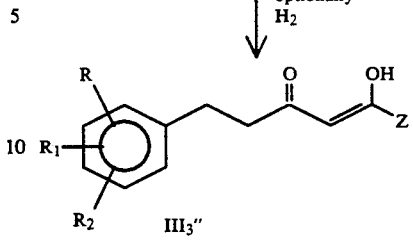

Finally, the compound of formula II$_2$ as shown in Scheme II above can be prepared by the following method.

SCHEME IX

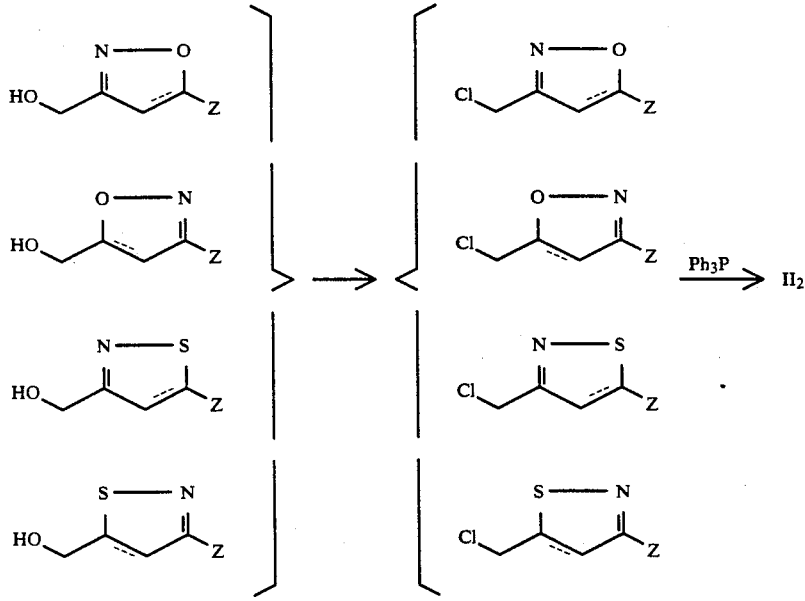

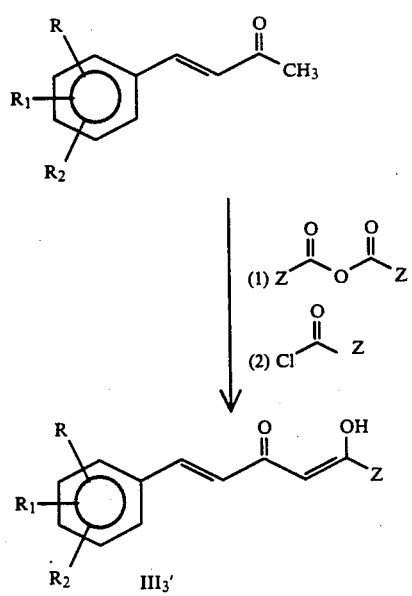

Under certain circumstances it is necessary to protect either the N or O of intermediates in the above noted process with suitable protecting groups which are known. Introduction and removal of such suitable oxygen and nitrogen protecting groups are well-known in the art of organic chemistry; see for example "Protective Groups in Organic Chemistry," J. F. W. McOmie, ed., (New York, 1973), pages 43ff, 95ff, J. F. W. McOmie, *Advances in Organic Chemistry*, Vol 3, 191–281 (1963); R. A. Borssonas, *Advances in Organic Chemistry*, Vol. 3, 159–190 (1963); and J. F. W. McOmie, Chem. & Ind., 603 (1979).

Examples of suitable oxygen protecting groups are benzyl, t-butyldimethylsily, ethoxyethyl, and the like. Protection of an N-H containing moiety is necessary for some of the processes described herein for the preparation of compounds of this invention. Suitable nitrogen protecting groups are benzyl, triphenylmethyl, trialkylsilyl, trichloroethylcarbamate, trichloroethoxycarbonyl, vinyloxycarbamate, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethylsilyl being removed by reaction with, for example, tetra-n-butylammonium fluoride.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

The products of the reactions described herein are isolated by conventional means such as extraction, distillation, chromatography, and the like.

Starting materials not described herein are available commercially, are known, or can be prepared by methods known in the art.

The salts of the compounds of formula I described above are prepared by reacting the appropriate base or acid with a stoichiometric equivalent of the compounds of formula I, respectively, to obtain pharmaceutically acceptable salts thereof.

DESCRIPTION OF THE PREFERRED EMBODIMENTS

The invention is further elaborated by the representative examples as follows. Such examples are not meant to be limiting.

EXAMPLE 1

3,5-Bis[$\beta$-(4'-hydroxy-3'-methoxyphenyl)ethenyl]-pyrazole

Curcumin (5.93 g, 16.1 mmoles) (Sigma Co., St. Louis) is dissolved in 100 ml of 50% ethanol in butanol. Hydrazine hydrate (0.81 g, 16.1 mmoles) and 0.5 ml of acetic acid are added. The reaction is warmed in an oil bath at 60° C. for 24 hours. The solvents are removed under vacuum, and the residue is chromatographed on silica gel in ethyl acetate to give a red solid. Recrystallization of the product from methanol/water gives 0.3 g of the product as a hydrate. Analysis for $C_{21}H_{20}N_2O_4 \cdot 0.1$ mole $H_2O$ requires C-68.87, H-5.52, N-7.65. Found; C-68.77, H-5.50, N-7.44. mp=211°-214° C.

EXAMPLE 2

3,5-Bis[$\beta$-(4'-hydroxy-3'-methoxyphenyl)ethyl]-pyrazole

According to the procedure of Example 1, 1,7-bis(4'-hydroxy-3'-methoxyphenyl)-3,5-heptadione (Bull. Acad. Polon. Sci. 6, 481-486, 1958) is reacted with hydrazine hydrate to afford 3,5-bis[$\beta$-(4'-hydroxy-3'-methoxyphenyl)ethyl]pyrazole in 65% yield, mp=125°-128° C.

EXAMPLE 3

3,5-Bis[$\beta$-(4'-hydroxyphenyl)ethyl]pyrazole

According to the procedure of Example 1, 1,7-bis(4'-hydroxyphenyl)-3,5-heptadione is reacted with hydrazine hydrate to afford 3,5-bis[$\beta$-(4'-hydroxyphenyl)ethyl]pyrazole in 45% yield, mp=193°-195° C.

EXAMPLE 4

3-[$\beta$-(4'-Hydroxy-3'-methoxyphenyl)ethenyl]-5-phenyl-pyrazole

According to the procedure of Example 1, 1-(4'-hydroxy-3'-methoxyphenyl)-5-phenyl-1-pentene-3,5-dione is reacted with hydrazine hydrate to afford 3-[$\beta$-(4'-hydroxy-3'-methoxyphenyl)ethenyl]-5-phenyl-pyrazole in 9% yield, mp=132°-134° C.

EXAMPLE 5

3-[$\beta$-(4'-Hydroxy-3'-methoxyphenyl)ethenyl]-5-methyl-pyrazole

According to the procedure of Example 1, 1-(4'-hydroxy-3'-methoxyphenyl)-1-hexene-3,5-dione is reacted with hydrazine hydrate to afford 3-[$\beta$-(4'-hydroxy-3'-methoxyphenyl)ethenyl]-5-methyl-pyrazole in 53% yield, mp=144°-146° C.

EXAMPLE 6

3-[$\beta$-(4'-Hydroxy-3'-methoxyphenyl)ethyl]-5-methyl-pyrazole

According to the procedure of Example 1, 1-(4'-hydroxy-3'-methoxyphenyl)-3,5-hexanedione is reacted with hydrazine hydrate to afford 3-[$\beta$-(4'-hydroxy-3'-methoxyphenyl)ethyl]-5-methyl-pyrazole in 68% yield, mp=84°-86° C.

EXAMPLE 7

3-[$\beta$-(4'-Hydroxy-3'-chlorophenyl)ethenyl]-5-methyl-pyrazole

According to the procedure of Example 1, 1-(4'-hydroxy-3'-chlorophenyl)-1-hexene-3,5-dione is reacted with hydrazine hydrate to afford 3-[$\beta$-(4'-hydroxy-3'-chlorophenyl)ethenyl]-5-methyl-pyrazole in 61% yield, mp=183°-184° C.

EXAMPLE 8

3-[$\beta$-(4'-Methoxy-3'-hydroxyphenyl)ethenyl]-5-methyl-pyrazole

According to the procedure of Example 1, 1-(4'-methoxy-3'-hydroxyphenyl)-1-hexene-3,5-dione is reacted with hydrazine hydrate to afford 3-[$\beta$-(4'-methoxy-3'-hydroxyphenyl)ethenyl]-5-methyl-pyrazole in 72% yield, mp=221°-222° C.

EXAMPLE 9

3-[$\beta$-(4'-Hydroxy-3'-methoxyphenyl)ethenyl]-5-ethyl-pyrazole

According to the procedure of Example 1, 1-(4'-hydroxy-3'-methoxyphenyl)-1-heptene-3,5-dione 25 is reacted with hydrazine hydrate to afford 3-[$\beta$-(4'-hydroxy-3'-methoxyphenyl)ethenyl]-5-ethyl-pyrazole in 26% yield, mp=61°-64° C.

EXAMPLE 10

Ethyl-3-[$\beta$-(3-methoxy-4-hydroxyphenyl)ethenyl]-1H-pyrazole-5-carboxylate

According to the procedure of Example 1, ethyl 6-(3-methoxy-4-hydroxyphenyl)-2,4-dioxo-5-hexenoate is reacted with hydrazine hydrate to afford ethyl-3-[$\beta$-(3-methoxy-4-hydroxyphenyl)ethenyl]-1H-pyrazole-5-carboxylate in 51% yield, mp=99°-101° C.

EXAMPLE 10A

3-[β-(4'-Hydroxy-3'-methoxyphenyl)ethenyl]-5-trifluoromethylpyrazole

According to the procedure of Example 1, 1-(4'-hydroxy-3'-methoxyphenyl)-6,6,6-trifluoro-1-hexene-3,5-dione is reacted with hydrazine hydrate to afford 3-[β-(4'-hydroxy-3'-methoxyphenyl)ethenyl]-5-trifluoromethylpyrazole in 71% yield, mp=145°-147° C.

EXAMPLE 10B

3-[β-(4'-t-Butyldimethylsilyloxy-3'-methoxyphenyl)ethenyl]-5-methylpyrazole

According to the procedure of Example 1, 1-(4'-t-butyldimethylsilyloxy-3'-methoxyphenyl)-1-hexene-3,5-dione is reacted with hydrazine hydrate to afford 3-[β-(4'-t-butyldimethylsilyloxy-3'-methoxyphenyl)ethenyl]-5-methylpyrazole in 52% yield, sufficiently pure for further use.

EXAMPLE 10C

3-[β-(4'-t-Butyldimethylsilyloxy-3,5-dimethoxyphenyl)ethenyl]-5-methylpyrazole

According to the procedure of Example 1, 1-(4'-t-butyldimethylsilyloxy-3',5'-dimethoxyphenyl)-1-hexene-3,5-dione is reacted with hydrazine hydrate to afford 3-[β-(4'-t-butyldimethylsilyloxy-3',5'-dimethoxyphenyl)ethenyl]-5-methylpyrazole in 32% yield, mp=133°-136° C.

EXAMPLE 10D (E)-5-[β-(4'-Hydroxy-3',5'-dimethoxyphenyl)ethenyl]-3-methyl-1H-pyrazole-1-acetic acid, ethyl ester A solution of 1-(4'-hydroxy-3',5'-dimethoxyphenyl)-1-hexene-3,5-dione (1.0 g, 3.8 mmol) in absolute ethanol (100 mL) is added to a solution of ethyl hydrazinoacetate in absolute ethanol (100 mL) according to the procedure found in A. Carmi et al, *J. Org. Chem.* 25, 44 (1960). The reaction mixture is acidified with acetic acid (2 mL) and is stirred for 30 minutes at room temperature. The solvent is evaporated, and the residue is suspended in water (50 mL). The solid which is collected is then purified by flash chromatography (silica gel, 1:1 methylenechloride/ethyl acetate) and subsequent recrystallization (methylenechloride/ethyl acetate 1:1) to afford 0.45 g (34%) of (E)-5-[β-(4'-hydroxy-3',5'-dimethoxyphenyl)ethenyl]-3-methyl-1H-pyrazole-1-acetic acid, ethyl ester, mp=159°-160° C. Analysis for $C_{18}H_{22}N_2O_5$. Calculated C-62.42, H-6.40, N-8.09. Found C-62.08, H-6.39, N-8.26.

EXAMPLE 10E

5-[β-(4'-t-Butyldimethylsilyloxy-3'-methoxyphenyl)ethenyl]-3-methyl-1H-pyrazole-1-acetic acid, methyl ester; and
3-[β-(4'-t-butyldimethylsilyloxy-3'-methoxyphenyl)ethenyl]-5-methyl-1H-pyrazole-1-acetic acid, methyl ester 3-[β-(4'-t-butyldimethylsilyloxy-3'-methoxyphenyl)ethenyl]-5-methylpyrazole (2.57 g, 7.5 mmol) is dissolved in DMF (20 mL). Potassium carbonate (10.30 g, 75 mmol) is ground into a fine powder and added to the reaction. The reaction is stirred at room temperature for 10 minutes under argon atmosphere. Methyl bromoacetate is added and the reaction is stirred for 2 hours. The mixture is then poured into water (200 mL) and neutralized with aqueous HCl. The layers are separated, and the aqueous layer is washed with methylenechloride. The combined organic layers are washed with water and brine. Drying over $MgSO_4$ followed by evaporation of solvents affords a brown oil. Flash chromatography (10% ethyl ether in methylenechloride) separates two products: 3-[β-(4'-t-butyldimethylsilyloxy-3'-methoxyphenyl)ethenyl]-5-methyl-1H-pyrazole-1-acetic acid, methyl ester (Rf=0.31); 1.5 g; and 5-[β-(4'-t-butyldimethylsilyloxy-3'-methoxyphenyl) ethenyl]-3-methyl-1H-pyrazole-1-acetic acid, methyl ester (Rf=0.14), 0.55 g.

EXAMPLE 10F

3-[β-(4'-t-butyldimethylsilyloxy-3',5'-dimethoxyphenyl)ethenyl]-5-methyl-1H-pyrazole-1-acetic acid, methyl ester and
5-[β-(4'-t-butyldimethylsilyloxy-3',5'-dimethoxyphenyl)ethenyl]-3-methyl-1H-pyrazole-1-acetic acid, methyl ester According to the procedure of Example 10E, 3-[β-(4'-t-butyldimethylsilyloxy-3',5'-dimethoxyphenyl)ethenyl]-5-methylpyrazole (3.5 g, 9.35 mmol) is reacted with methyl bromoacetate to afford 3-[β-(4'-t-butyldimethylsilyloxy-3',5'-dimethoxyphenyl)ethenyl]-5-methyl-1H-pyrazole-1-acetic acid, methyl ester, 2.3 g (55%), mp=139°-141° C.; and 5-[β-(4'-t-butyldimethylsilyloxy-3',5'-dimethoxyphenyl)ethenyl]-3-methyl-1H-pyrazole-1-acetic acid, methyl ester, 0.9 g (21%), mp=150°-151° C.

EXAMPLE 10G

3-[β-(4'-Hydroxy-3',5'-di-t-butylphenyl)ethenyl]-5-methyl-1H-pyrazole-1-acetic acid, methyl ester and
5-[β-(4'-Hydroxy-3',5'-di-t-butylphenyl)ethenyl]-3-methyl-1H-pyrazole-1-acetic acid, methyl ester According to the procedure of Example 10E, 3-[β-(4'-hydroxy-3',5'-di-t-butylphenyl)ethenyl]-5-methylpyrazole (3.0 g, 9.6 mmol) is reacted with methyl bromoacetate in DMF, with the exception that sodium acetate is used in place of potassium carbonate. Flash chromatography separates 3-[β-(4'-hydroxy-3',5'-di-t-butylphenyl)ethenyl]-5-methyl-1H-pyrazole-1-acetic acid, methyl ester, 0.65 g (18%), mp=170°-174° C.; and 5-[β-(4'-hydroxy-3',5'-di-t-butylphenyl)ethenyl]-3-methyl-1H-pyrazole-1-acetic acid, methyl ester, (as HCl salt) 0.72 g (17%), mp=179°-180° C. Analysis for $C_{23}H_{33}ClN_2O_3$. Calculated C-65.62, H-7.90, N-6.65, Cl-8.42. Found C-65.53, H-7.99, N-6.46, Cl-8.31.

EXAMPLE 10G

3-[β-(4'-Hydroxy-3',5'-di-t-butylphenyl)ethenyl]-1,5-dimethylpyrazole and
5-[β-(4'-hydroxy-3',5'-di-t-butylphenyl)ethenyl]-1,3-dimethylpyrazole According to the procedure of Example 10G, 3-[β-(4'-hydroxy-3',5'-di-t-butylphenyl)ethenyl]-5-methylpyrazole is reacted with methyl iodide and sodium acetate to afford two regioisomeric products separated by flash chromatography (chloroform): 3-[β-(4'-hydroxy-3',5'-di-t-butylphenyl)ethenyl]-1,5-dimethylpyrazole (%), mp=155°-157° C.; 3-[β-(4'-hydroxy-3',5'-di-t-butylphenyl)ethenyl]-1,3-dimethylpyrazole (%), mp=120°-122° C.

EXAMPLE 10H

3-[β-(4'-Hydroxy-3',5'-dimethoxyphenyl)ethenyl]-5-methyl-1H-pyrazole-1-acetic acid, methyl ester To a solution of 3-[β-(4'-t-butyldimethylsilyloxy-3',5'-dimethoxyphenyl)ethenyl]-5-methyl-1H-pyrazole-1-acetic acid, methyl ester (2.25 g, 5.0 mmol) in dry THF (150 mL) is added tetra-n-butylammonium fluoride (7.5 mL, 1M solution in THF) at 0° C. The reaction mixture is stirred at 0° C. for one hour and then quenched by the dropwise addition of brine (100 mL) at 0° C. The layers are separated and the aqueous layer extracted with ethyl acetate. The combined organic layers are evaporated and the residue purified by flash chromatography (ethyl acetate/methylene chloride 1:1) to afford 1.35 g (80%) of 3-[β-(4'-hydroxy-3',5'-dimethoxyphenyl) ethenyl]-5-methyl-1H-pyrazole-1-acetic acid methyl ester, mp=112°-114° C. Analysis for $C_{17}H_{20}N_2O_5$. Calculated C-61.44, H-6.07, N-8.43. Found C-61.23, H-6.08, N-8.44.

EXAMPLE 10I

5-[β-(4'-Hydroxy-3'-methoxyphenyl)ethenyl]-3-methyl-1H-pyrazole-1-acetic acid methyl ester According to the procedure of Example 10H, 5-[β-(4'-t-butyldimethylsilyloxy-3'-methoxyphenyl) ethenyl]-3-methyl-1H-pyrazole-1-acetic acid methyl ester is reacted with tetra-n-butyl ammonium fluoride to afford 5-[β-(4'-hydroxy-3'-methoxyphenyl)ethenyl]-3-methyl-1H-pyrazole-1-acetic acid methyl ester, in 46% yield, mp=159°-160° C. Analysis for $C_{16}H_{18}N_2O_4$. Calculated C-63.55, H-6.01, N-9.27. Found C-63.68, H-6.05, N-9.20.

EXAMPLE 10J

3-[β-(4'-Hydroxy-3'-methoxyphenyl)ethenyl]-5-methyl-1H-pyrazole-1-acetic acid, methyl ester According to the procedure of Example 10H, 3-[β-(4'-t-butyldimethylsilyloxy-3'-methoxyphenyl) ethenyl]-5-methyl-1H-pyrazole-1-acetic acid methyl ester is reacted with tetra-n-butyl ammonium fluoride to afford 3-[β-(4'-hydroxy-3'-methoxyphenyl)ethenyl]-5-methyl-1H-pyrazole-1-acetic acid methyl ester, in 78% yield, mp=141°-143° C. Analysis for $C_{16}H_{18}N_2O_4$. Calculated C-63.55, H-6.01, N-9.27. Found C-63.53, H-6.02, N-8.89.

EXAMPLE 10K

3-[β-(4'-Hydroxy-3'-methoxyphenyl)ethenyl]-5-methyl-1H-pyrazole-1-acetic acid

A solution of 3-[β-(4'-hydroxy-3'-methoxyphenyl) ethenyl]-5-methyl-1H-pyrazole-1-acetic acid methyl ester (1.1 g, 3.6 mmol) in aqueous sodium hydroxide (200 mL, 1N solution) with the minimum amount of hot ethanol needed for dissolution, is heated on a steam bath for 2 hours. The reaction mixture is cooled and neutralized with 4N HCl. The resulting precipitate is collected by filtration and recrystallized from 2-propanol/water to afford 3-[β-(4'-hydroxy-3'-methoxyphenyl)ethenyl]-5-methyl-1H-pyrazole-1-acetic acid, 0.64 g (62%), mp=225°-232° C. Analysis for $C_{15}H_{16}N_2O_4$. Calculated C-62.49, H-5.59, N-9.72. Found C-62.35, H-5.64, N-9.69.

EXAMPLE 10L

5-[β-(4'-Hydroxy-3'-methoxyphenyl)ethenyl]-3-methyl-1H-pyrazole-1-acetic acid

According to the procedure of Example 10K, 5-[β-(4'-hydroxy-3'-methoxyphenyl)ethenyl]-3-methyl-1H-pyrazole-1-acetic acid methyl ester is saponified to afford 5-[β-(4'-hydroxy-3'-methoxyphenyl)ethenyl]-3-methyl-1H-pyrazole-1-acetic acid, in 71% yield. Mp=265°-268° C. Analysis for $C_{15}H_{16}N_2O_4$. Calculated C-62.49, H-5.59, N-9.72. Found C-62.26, H-5.58, N-9.56.

EXAMPLE 10M

5-[β-(4'-Hydroxy-3',5'-dimethoxyphenyl)ethenyl]-3-methyl-1H-pyrazole-1-acetic acid According to the procedure of Example 10K, 5-[β-(4'-hydroxy-3',5'-dimethoxyphenyl)ethenyl]-3-methyl-1H-pyrazole-1-acetic acid methyl ester is saponified to afford 5-[β-(4'-hydroxy-3',5'-dimethoxyphenyl)ethenyl]-3-methyl-1H-pyrazole-1-acetic acid, in 90% yield. Mp=240°-243° C. Analysis for $C_{16}H_{18}N_2O_5 \cdot 0.1 H_2O$. Calculated C-60.03, H-5.73, N-8.75. Found C-59.90, H-5.50, N-8.66.

EXAMPLE 10N

3-[β-(4'-Hydroxy-3',5'-dimethoxyphenyl)ethenyl]-5-methyl-1H-pyrazole-1-acetic acid According to the procedure of Example 10K, 3-[β-(4'-hydroxy-3',5'-dimethoxyphenyl)ethenyl]-5-methyl-1H-pyrazole-1-acetic acid methyl ester is saponified to afford 3-[β-4'-hydroxy-3',5'-dimethoxyphenyl)ethenyl]-5-methyl-1H-pyrazole-1-acetic acid, in 65% yield. Mp=232°-234° C. Analysis for $C_{16}H_{18}N_2O_5$. Calculated C-60.37, H-5.70, N-8.80. Found C-60.20, H-5.88, N-8.53.

EXAMPLE 10P

5-[β-(4'-Hydroxy-3',5'-di-t-butylphenyl)ethenyl]-3-methyl-1H-pyrazole-1-acetic acid According to the procedure of Example 10K, 5-[β-(4'-hydroxy-3',5'-di-t-butylphenyl)ethenyl]-3-methyl-1H-pyrazole-1-acetic acid methyl ester is saponified to afford 5-[β-(4'-hydroxy-3',5'-di-t-butylphenyl)ethenyl]-3-methyl-1H-pyrazole-1-acetic acid, in 50% yield. Mp=220°-224° C. Analysis for $C_{22}H_{30}N_2O_3$. Calculated C-71.32, H-8.16, N-7.56. Found C-71.14, H-8.16, N-7.46.

EXAMPLE 10Q

3-[β-(4'-Hydroxy-3',5'-di-t-butylphenyl)ethenyl]-5-methyl-1H-pyrazole-1-acetic acid According to the procedure of Example 10K, 3-[β-(4'-hydroxy-3',5'-di-t-butylphenyl)ethenyl]-5-methyl-1H-pyrazole-1-acetic acid methyl ester is saponified to afford 3-[β-(4'-hydroxy-3',5'-di-t-butylphenyl)ethenyl]-5-methyl-1H-pyrazole-1-acetic acid, in 50% yield. Mp=227°-229° C. Analysis for $C_{22}H_{30}N_2O_3$. Calculated C-71.32, H-8.16, N-7.56. Found C-71.22, H-8.18, N-7.53.

EXAMPLE 11

3-[β-(3-Methoxy-4-hydroxyphenyl)ethenyl]-1H-pyrazole-5-carboxylic acid

Ethyl-3-[β-(3-methoxy-4-hydroxyphenyl)ethenyl]-1H-pyrazole-5-carboxylate (0.49 g, 1.7 mmoles) is added to a solution of KOH (0.38 g, 6.8 mmoles) in 0 ml EtOH. The reaction is warmed to reflux overnight. After cooling to room temperature, the reaction is diluted to 200 ml with $H_2O$, and acidified to pH=4 with HCl. A white precipitate forms, and it is collected by filtration. Drying in vacuum in the presence of $P_2O_5$ gives 0.3 g (68%) of the desired product, mp=270°–271° C. (dec).

EXAMPLE 12

3,5-Bis[β-(4'-hydroxy-3'-methoxyphenyl)ethyl]-isoxazole 1,7-Bis(4'-hydroxy-3'-methoxyphenyl)-3,5-heptadione (1.00 g, 2.7 mmoles) (Bull. Acad. Polon. Sci. 6, 481–486, 1958), hydroxylaminehydrochloride (0.19 g, 2.7 mmoles), and sodium acetate (0.44 g, 5.4 mmoles) are dissolved in 50 ml of 95% ethanol. The reaction is stirred at reflux overnight. The solvent is removed, and the residue is taken up in ethyl acetate. The ethyl acetate solution is washed with water and dried over magnesium sulfate. A precipitate forms on standing at room temperature for 2 days, and it is collected by filtration to give a white solid. The solid is taken up in 20 ml of ethanol containing 0.5 ml of 2N hydrochloric acid. The solution is heated to reflux for one hour. After neutralization with sodium bicarbonate, the ethanol is evaporated, and the residue is partitioned between ethyl acetate and water. The organic layer is dried over magnesium sulfate and passed through a silica gel plug which is washed with 1:1 ethyl acetate/hexane. Evaporation of the solvent gives 0.2 g of the product obtained as a hydrate. mp=106°–107° C. Analysis for $C_{21}H_{25}NO_6 \cdot 0.4$ mole $H_2O$. Calculated C-66.97, H-6.38, N-3.72. Found C-67.13, H-6.41, N-3.47.

EXAMPLE 13

5-[β-(4'-Acetoxy-3'-methoxyphenyl)ethenyl]-3-trifluoromethylisoxazole

To a solution of isoxazole-3-trifluoromethyl-5-methyltriphenylphosphonium chloride (350 mg, 0.78 mmol) in dimethylsulfoxide (5 ml) is added potassium t-butoxide (120 mg, 1.10 mmol). The mixture is stirred at room temperature for 45 minutes under an inert atmosphere. Acetylvanillin (170 mg, 0.89 mmol) is then added and the reaction stirred an additional one hour. The mixture is poured into saturated aqueous ammonium chloride and extracted into ethyl acetate. The organic layer is washed with water and dried over magnesium sulfate. Concentration and flash chromatography (hexane/ethyl acetate 3:1) afforded 150 mg of 5-[β-(4'-acetoxy-3'-methoxyphenyl)ethenyl]-3-trifluoromethylisoxazole, of sufficient purity for subsequent reaction.

EXAMPLE 13A (E)-5-[β-(4'-Hydroxy-3',5'-bis(1,1-dimethylethyl)phenyl)ethenyl]-3-trifluoromethylisoxazole According to the procedure of Example 13, potassium t-butoxide (264 mg), isoxazole-3-trifluoromethyl-5-methyl triphenylphosphonium chloride (1.054 g), and 3,5-di-t-butyl-4-hydroxybenzaldehyde (250 mg) are reacted in DMSO for 24 hr at room temperature to afford a cis-/trans-mixture of two olefinic products. Refluxing a mixture of this isomeric mixture in HCl/methanol (12 hrs) affords pure (E)-5-[β-(4'-hydroxy-3',5'-bis(1,1-dimethylethyl)phenyl)ethenyl]-3-trifluoromethylisoxazole (350 mg); mp=132°–134° C. Analysis for $C_{20}H_{24}NO_2F_3$. Calculated C-65.38, H-6.58, N-3.81. Found C-65.58, H-6.68, N-3.92.

EXAMPLE 14

5-[β-(4'-Hydroxy-3'-methoxyphenyl)ethenyl]-3-trifluoromethylisoxazole

A solution of 5-[β-(4'-acetoxy-3'-methoxyphenyl)ethenyl]-3-trifluoromethylisoxazole (120 mg, 0.34 mmol) in methanol (3 ml) is cooled to 0° C. Sodium methoxide (40 mg, 0.68 mmol) is added and the mixture stirred for 30 minutes. The mixture is diluted with ethyl acetate and washed with water. The organic layer is dried (magnesium sulfate) and concentrated. Recrystallization from hexane/ethyl acetate affords 80 mg of pure 5-[β-(4'-hydroxy-3'-methoxyphenyl)ethenyl]-3-trifluoromethylisoxazole; yield 82%; mp=83°–87° C.

EXAMPLE 15

1,7-Bis-(4'-hydroxyphenyl)-3,5-heptadione

A solution of 1,7-bis-(4'-hydroxyphenyl)-1,6-heptadiene-3,5-dione (1.99 g, 6.5 mmoles) in tetrahydrofuran (100 ml) is hydrogenated over Raney-nickel (0.2 g) under 30.4 psi of $H_2$. The THF is evaporated, and the residue chromatographed in 5% $MeOH/CHCl_3$ to give 1.6 g (79%) of the desired product, mp=108°–110° C.

EXAMPLE 16

1-(3'-Methoxy-4'-hydroxyphenyl)hexane-3,5-dione

According to the procedure of Example 15, 1-(3'-methoxy-4'-hydroxyphenyl)-1-hexene-3,5-dione is hydrogenated to afford in 90% yield 1-(3'-methoxy-4'-hydroxyphenyl)hexane-3,5-dione as an oil.

EXAMPLE 17

1-(4'-Hydroxy-3'-methoxyphenyl)-1-hexene-3,5-dione

Boric anhydride (16.32 g, 237.2 mmoles) and acetylacetone are stirred at room temperature under nitrogen for 12 hours. 4-Hydroxy-3-methoxybenzaldehyde (18.06 g, 118.8 mmoles) and tributyl borate (364 g, 3.16 moles) are combined with the acetyl acetone/boric anhydride complex in 100 ml of ethyl acetate. The reaction is stirred at room temperature for one hour, at which time n-butylamine (4.34 g, 59.4 mmoles) is added in 4 equal portions over 8 hours. The reaction is allowed to stir for 12 hours. 300 ml of water containing 20 ml of concentrated hydrochloric acid is added to the reaction and stirred for 2 hours. The solid which forms is removed by filtration through celite, and the layers of filtrate are separated. The ethyl acetate layer is washed with 2×100 ml of saturated sodium bicarbonate, followed by 100 ml of brine. Drying over magnesium sulfate followed by evaporation of the solvent gives a red solid. Chromatography in 5% ethyl acetate/chloroform gives 11.06 g (40%) of a yellow solid. mp=146°–147° C. Analysis for $C_{13}H_{14}O_4$ requires C-66.65, H-6.04. Found C-66.88, H-6.18.

The following compounds were made by the above procedure:

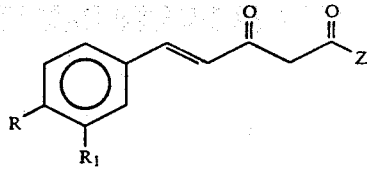

| Ex. | R | $R_1$ | Z | Melting Point | Yield |
|---|---|---|---|---|---|
| 18 | HO | Cl | Me | 155–157° C. | 14% |
| 19 | MeO | HO | Me | 160–162° C. | 13% |
| 20 | HO | MeO |  [1] | 155–157° C. | 75% |
| 21 | HO | MeO | Et [2] | 101–102° C. | 21% |

[1] From 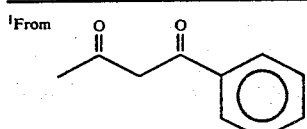

[2] From 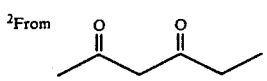

EXAMPLE 22

Ethyl 6-(3'-methoxy-4'-hydroxyphenyl)-2,4-dioxo-5-hexenoate

Sodium metal (1.8 g, 0.078 mole) is dissolved in absolute ethanol (50 ml) under an inert atmosphere. An ethanolic solution of 1-(3'-methoxy-4'-hydroxyphenyl)-1-butene-3-one (5.00 g, 0.026 mole) is then added slowly to the sodium ethoxide solution. The mixture is stirred for 10 minutes, after which diethyl oxalate (3.80 g, 0.026 mole) is added. The reaction is stirred at room temperature for 5 hours and then acidified with concentrated HCl. The mixture is then stirred at 0° C. for 1 hour. The precipitate is collected and dried to afford 4.8 g of ethyl 6-(3'-methoxy-4'-hydroxyphenyl)-2,4-dioxo-5-hexenoate; 63% yield; mp=97°-98° C.

EXAMPLE 22A 1-(4'-t-Butyldimethylsilyloxy-3'-methoxyphenyl)-1-hexene-3,5-dione A solution of 1-(4'-t-butyldimethylsilyloxy-3'-methoxyphenyl)-1-butene-3-one (12.8 g, 41.8 mmol) in THF (50 mL) is cooled to −78° C. under an argon atmosphere. Lithium di-isopropyl amide (83.5 mmol, in 50 mL THF) is slowly added to the reaction mixture. The reaction is stirred at −78° C. for 30 minutes. Acetyl chloride (16.4 g, 209 mmol) dissolved in THF (20 mL) is then added to the reaction over a 30 minute period. The reaction is quenched with aqueous HCl. The layers are separated, and the aqueous layer is washed with ethyl acetate. The combined organic layers are washed with saturated aqueous sodium bicarbonate, dried over MgSO$_4$, and evaporated to give a red oil. Flash chromatography (ethyl ether/hexane 2:8) afford 5.0 g (34%) of 1-(4'-t-butyldimethylsilyloxy-3'-methoxyphenyl)-1-hexene-3,5-dione, mp=81°-85° C.

EXAMPLE 22B 1-(4'-Hydroxy-3'-methoxyphenyl)-6,6,6-trifluoro-1-hexene-3,5-dione According to the procedure of Example 22A, 1-(4'-hydroxy-3'-methoxyphenyl)-1-butene-3-one is reacted with lithium di-isopropylamide (3.0 equiv) and trifluoroacetic anhydride (2.0 equiv) to afford 1-(4'-hydroxy-3'-methoxyphenyl)-6,6,6-trifluoro-1-hexene-3,5-dione in 10% yield, mp=97°-100° C.

EXAMPLE 22C 1-(4'-t-Butyldimethylsilyloxy-3'-methoxyphenyl)-1-butene-3-one

To a methylene chloride (100 mL) solution of 1-(4'-hydroxy-3'-methoxyphenyl)-1-butene-3-one (10.0 g, 52 mmol) is added triethyl amine (5.8 g, 57.2 mmol) and t-butylchlorodimethyl silane (15.7 g, 104 mmol). The reaction is stirred at room temperature for 12 hours under an argon atmosphere. The mixture is washed with water (3×100 mL) and brine (100 mL). The organic layer is dried over MgSO$_4$ and evaporated. Flash chromatography (ethyl ether/hexane 1:1) affords 12.8 g (80%) of the desired 1-(4'-t-butyldimethylsilyloxy-3'-methoxyphenyl)-1-butene-3-one, mp=65°-68° C.

EXAMPLE 22D 1-(4'-t-Butyldimethylsilyloxy-3',5'-dimethoxyphenyl)-1-hexene-3,5-dione According to the procedure of Example 22C, 1-(4'-hydroxy-3',5'-dimethoxyphenyl)-1-hexene-3,5-dione is reacted with t-butylchlorodimethyl silane to afford 1-(4'-t-butyldimethylsilyloxy-3',5'-dimethoxyphenyl)-1-hexene-3,5-dione suitably pure for further use.

EXAMPLE 23

5-Chloromethyl-3-trifluoromethylisoxazole

A solution of 3-trifluoromethyl-5-hydroxymethylisoxazole [(700 mg, 4.2 mmol) See K. Tanaka et al, *Bull. Chem. Soc. Jpn.*, 57, 2184 (1984)] and triphenylphosphine (1.43 g, 5.4 mmol) in carbontetrachloride (50 ml) and dichloromethane (20 ml) is heated at reflux for 6 hours. The reaction mixture is then cooled to room temperature and passed through a silica gel plug. Concentration affords in 82% yield the desired 5-chloromethyl-3-trifluoromethylisoxazole of sufficient purity for the following step (Example 24).

EXAMPLE 24

Isoxazole, 3-trifluoromethyl-5-methyltriphenylphosphonium chloride

Triphenylphosphine (1.016 g, 3.9 mmol) and 5-chloromethyl-3-trifluoromethylisoxazole (0.72 g, 3.9 mmol) are dissolved in toluene (40 ml) and heated at reflux for 24 hours. Upon cooling, a white precipitate formed and was filtered to afford in 60% yield the desired isoxazole, 3-trifluoromethyl-5-methyltriphenylphosphonium chloride, mp=245°-250° C.

EXAMPLE 25

5-Isoxazoleethanol,
α-[3,5-bis(1,1-dimethylethyl)-4-hydroxyphenyl]-3-methyl- 3,5-Dimethylisoxazole (26 g, $2.7 \times 10^{-1}$M) is dissolved in dry THF (100 ml) and cooled to $-78°$ C. with an acetone dry ice bath. n-Butyllithium ($2.7 \times 10^{-1}$M) is added dropwise via a syringe. The 3,5-dimethylisoxazole, n-butyllithium mixture is stirred at $-78°$ C. for two hours under an argon atmosphere. 3,5-Di-tert-butyl-4-hydroxybenzaldehyde (18 g, $17.68 \times 10^{-2}$ M) is dissolved in dry THF (200 ml) and added dropwise via cannula under an argon atmosphere to the 3,5-dimethylisoxazole and n-butyllithium mixture. The reaction mixture is allowed to warm to room temperature and is stirred for an additional eight hours. The reaction mixture is evaporated to near dryness, redissolved in ethyl acetate (500 ml), washed with distilled water, then brine. The organic phase is dried over sodium sulfate, filtered, evaporated to dryness, and chromatographed on flash silica using hexane:ethyl acetate 3:2 to give 16.8 g (70% yield) of the desired 5-isoxazoleethanol, α-[3,5-bis(1,1-dimethylethyl)-4-hydroxyphenyl]-3-methyl-; mp=145°-147° C. Analysis for $C_{20}H_{29}O_3N$ (331.46). Calculated C-72.47, H-8.81, N-4.22. Found C-72.31, H-8.84, N-4.24.

EXAMPLE 25A

5-Isoxazoleethanol, α-[4-hydroxyphenyl]-3-methyl-

According to the procedure of Example 25, 3,5-dimethylisoxazole is reacted with 4-hydroxybenzaldehyde to afford 5-isoxazoleethanol, α-[4-hydroxyphenyl]-3-methyl-, pure enough for subsequent use.

EXAMPLE 25B

5-Isoxazoleethanol,
α-[3,5-dimethyl-4-hydroxyphenyl]-3-methyl-

According to the procedure of Example 25, 3,5-dimethylisoxazole is reacted with 3,5-dimethyl-4-hydroxybenzaldehyde to afford 5-isoxazoleethanol, α-[3,5-dimethyl-4-hydroxyphenyl]-3-methyl-, in 31% yield.

EXAMPLE 25C

5-Isoxazoleethanol,
α-[3,5-bis(1,1-dimethylethyl)-4-hydroxyphenyl]-3-phenyl-

According to the procedure of Example 25, 3-phenyl-5-methylisoxazole is reacted with 3,5-bis(1,1-dimethylethyl)-4-hydroxybenzaldehyde to afford 5-isoxazoleethanol, α-[3,5-bis(1,1-dimethylethyl)-4-hydroxyphenyl]-3-phenyl-, in 33% yield.

EXAMPLE 25D

5-Isoxazoleethanol, α-[3,5-dimethoxy-4-hydroxyphenyl]-3-phenyl-

According to the procedure of Example 25, 3-phenyl-5-methylisoxazole is reacted with 3,5-dimethoxy-4-hydroxybenzaldehyde to afford 5-isoxazoleethanol, α-[3,5-dimethoxy-4-hydroxyphenyl]-3-phenyl-, in 30% yield.

EXAMPLE 25E

5-Isoxazoleethanol,
α-[3-methoxy-4-hydroxyphenyl]-3-phenyl-

According to the procedure of Example 25, 3-phenyl-5-methylisoxazole is reacted with vanillin to afford 5-isoxazoleethanol, α-[3-methoxy-4-hydroxyphenyl]-3-phenyl-, in 41% yield.

EXAMPLE 25F

5-Isoxazoleethanol,
α-[3,5-dibromo-4-hydroxyphenyl]-3-methyl-

According to the procedure of Example 25, 3,5-dimethylisoxazole is reacted with 3,5-dibromo-4-hydroxybenzaldehyde to afford 5-isoxazoleethanol, α-[3,5-dibromo-4-hydroxyphenyl]-3-methyl-, in 53% yield. Mp=139°-143° C.

EXAMPLE 25G

5-Isoxazoleethanol,
α-[3,5-dichloro-4-hydroxyphenyl]-3-methyl-

According to the procedure of Example 25, 3,5-dimethylisoxazole is reacted with 3,5-dichloro-4-hydroxybenzaldehyde to afford 5-isoxazoleethanol, α-[3,5-dichloro-4-hydroxyphenyl]-3-methyl-, in 61% yield. Mp=129°-131° C.

EXAMPLE 25H

5-Isoxazoleethanol,
α-[2-hydroxy-3-methoxyphenyl]-3-methyl-

According to the procedure of Example 25, 3,5-dimethylisoxazole is reacted with 2-hydroxy-3-methoxybenzaldehyde to afford 5-isoxazoleethanol, α-[2-hydroxy-3-methoxyphenyl]-3-methyl-, as an oil in yield.

EXAMPLE 25J

5-Isoxazoleethanol,
α-[2-hydroxy-3,5-dibromophenyl]-3-methyl-

According to the procedure of Example 25, 3,5-dimethylisoxazole is reacted with 3,5-dibromosalicylaldehyde to afford 5-isoxazoleethanol, α-[2-hydroxy-3,5-dibromophenyl]-3-methyl-, in 47% yield.

EXAMPLE 25K

5-Isoxazoleethanol,
α-[2-hydroxy-3,5-dichlorophenyl]-3-methyl-

According to the procedure of Example 25, 3,5-dimethylisoxazole is reacted with 3,5-dichlorosalicylaldehyde to afford 5-isoxazoleethanol, α-[2-hydroxy-3,5-dichlorophenyl]-3-methyl- in 74% yield, mp=151°-153° C.

EXAMPLE 26

5-Isoxazoleethanol,
α-(4-hydroxy-3-methoxyphenyl)-3-methyl-

According to the procedure of Example 25, 3,5-dimethylisoxazole (10 g, 0.103 mole) is reacted with n-butyllithium (0.103 mole) and vanillin (7.8 g, 0.0515 mole) to afford 5-isoxazoleethanol, α-(4-hydroxy-3-methoxyphenyl)-3-methyl- (10 g, 78%); mp=128°-135° C.

EXAMPLE 27

5-Isoxazoleethanol,
α-(4-hydroxy-3,5-bis(1-methylethyl)phenyl)-3-methyl-

According to the procedure of Example 25, 3,5-dimethylisoxazole (11.5 g, 0.049 mole) is reacted with n-butyllithium (0.049 mole) and 3,5-bis(1-methylethyl)-4-hydroxybenzaldehyde (5 g, 0.0243 mole) to afford 5-isoxazoleethanol, α-(4-hydroxy-3,5-bis(1-methylethyl)phenyl)-3-methyl- (4.0 g, 56%); mp=79° C.

EXAMPLE 28

5-Isoxazoleethanol,
α-(4-hydroxy-3,5-dimethoxyphenyl)-3-methyl-

According to the procedure of Example 25, 3,5-dimethylisoxazole (4.26 g, 0.044 mole) is reacted with n-butyllithium (0.044 mole) and 4-hydroxy-3,5-dimethoxybenzaldehyde (4.00 g, 0.022 mole) to afford 5-isoxazoleethanol, α-(4-hydroxy-3,5-dimethoxyphenyl)-3-methyl- (3.82 g, 63%); mp=142° C.

EXAMPLE 29

5-[β-(4'-Hydroxy-3',5'-bis(1,1-dimethylethyl)phenyl)ethenyl]-3-methylisoxazole

A solution of 5-isoxazoleethanol, α-[3,5-bis(1,1-dimethylethyl)-4-hydroxyphenyl]-3-methyl- (16.8 g, 0.0507 mole) in HCl-saturated methanol (300 mL) is refluxed for 24 hr. The reaction mixture is evaporated to dryness, redissolved in ethyl acetate (400 mL), neutralized with 15% aqueous sodium bicarbonate and washed with brine. The residual organics are then dried (sodium sulfate) and concentrated to give a residue. Flash chromatography (hexane/ethyl acetate 3:1) affords 11.0 g of 5-[β-(4'-hydroxy-3',5'-bis(1,1-dimethylethyl)phenyl)ethenyl]-3-methylisoxazole; mp=174°-175° C. Calculated C-76.64, H, 8.68, N, 4.47. Found C-76.60; H, 8.62; N, 4.33.

EXAMPLE 30

5-[β-(4'-Hydroxy-3'-methoxyphenyl]ethenyl]-3-methylisoxazole

According to the procedure of Example 29, 5-isoxazoleethanol, α-(4-hydroxy-3-methoxyphenyl)-3-methyl- (10 g, 0.04 mole) is reacted with HCl-methanol to afford 5-[β-(4'-hydroxy-3'-methoxyphenyl)ethenyl]-3-methylisoxazole (7.5 g, 80%); mp=123°-127° C. Calculated C-67.52, H-5.67, N-6.06. Found C-67.14, H-5.68, N-5.96.

EXAMPLE 31

5-[β-(4'-Hydroxy-3',5'-bis(1-methylethyl)phenyl)ethenyl]-3-methylisoxazole

According to the procedure of Example 29, 5-isoxazoleethanol, α-(4-hydroxy-3,5-bis(1-methylethyl)phenyl)-3-methyl- (4.0 g, 0.013 mole) is reacted with HCl-methanol to afford 5-[β-(4-hydroxy-3',5'-bis(1-methylethyl)phenyl)ethenyl]-3-methyl-isoxazole (3.9 g, 98%); mp=119°-120° C. Calculated C-75.76, H-8.12, N-4.91. Found C-75.68, H-8.16, N-4.96.

EXAMPLE 32

5-[β-(4'-Hydroxy-3',5'-dimethoxyphenyl)ethenyl]-3-methylisoxazole

According to the procedure of Example 29, 5-isoxazoleethanol, α-(4-hydroxy-3,5-dimethoxy phenyl)-3-methyl- (3.00 g, 10.7 mmole) is reacted with HCl-methanol to afford 5-[β-(4'-hydroxy-3',5'-dimethoxyphenyl)ethenyl]-3-methylisoxazole (1.92 g, 69%); mp=152°-157° C. Calculated C-64.36, H-5.79, N-5.36. Found C-64.30, H-5.74, N-5.34.

EXAMPLE 32A

5-[β-(4'-Hydroxyphenyl)ethenyl]-3-methylisoxazole

According to the procedure of Example 29, 5-isoxazoleethanol, α-[4-hydroxyphenyl]-3-methyl- is reacted with HCl-methanol to afford 5-[β-(4'-hydroxyphenyl)ethenyl]-3-methylisoxazole (6.74 g, 14%); mp=17°-119° C.

EXAMPLE 32B

5-[β-(4'-Hydroxy-3',5'-dimethylphenyl)ethenyl]-3-methylisoxazole

According to the procedure of Example 29, 5-isoxazoleethanol, α-[3,5-dimethyl-4-hydroxyphenyl]-3-methyl- is reacted with HCl-methanol to afford 5-[β-(4'-hydroxy-3',5'-dimethylphenyl)ethenyl]-3-methylisoxazole (0.62 g, 85%); mp=158°-161° C. Analysis for $C_{14}H_{15}NO_2$. Calculated C-73.34, H-6.59, N-6.10. Found C-73.35, H-6.44, N-6.05.

EXAMPLE 32C

5-[β-(4'-Hydroxy-3',5'-bis(1,1-dimethylethyl)phenyl)ethenyl]-3-phenylisoxazole

According to the procedure of Example 29, 5-isoxazoleethanol, α-[3,5-bis(1,1-dimethylethyl)-4-hydroxyphenyl]-3-phenyl- is reacted with HCl-methanol to afford 5-[β-(4'-hydroxy-3',5'-bis(1,1-dimethyl-ethyl)phenyl) ethenyl]-3-phenylisoxazole (0.35 g, 90%); mp=157°-161° C. Analysis for $C_{25}H_{29}NO_2$. Calculated C-79.96, H-7.78, N-3.73. Found C-79.78, H-7.74, N-3.71.

EXAMPLE 32D

5-[β-(4'-Hydroxy-3',5'-dimethoxyphenyl)ethenyl]-3-phenylisoxazole

According to the procedure of Example 29, 5-isoxazoleethanol, c-[3,5-dimethoxy-4-hydroxyphenyl]-3-phenyl- is reacted with HCl-methanol to afford 5-[β-(4'-hydroxy-3',5'-dimethoxyphenyl) ethenyl]-3-phenylisoxazole (1.1 g, 95%); mp=135°-140° C. Analysis for $C_{19}H_{17}NO_4$. Calculated C-70.58, H-5.30, N-4.33. Found C-70.70, H-5.17, N-4.25.

EXAMPLE 32E

5-[β-(4'-Hydroxy-3'-methoxyphenyl)ethenyl]-3-phenyl isoxazole

According to the procedure of Example 29, 5-isoxazoleethanol, c-[3-methoxy-4-hydroxyphenyl]-3-phenyl- is reacted with HCl-methanol to afford 5-[β-(4'-hydroxy-3'-methoxyphenyl)ethenyl]-3-phenylisoxazole (1.0 g, 95%) mp=148°-152° C. Analysis for $C_{18}H_{15}NO_3$. Calculated C-73.71, H-5.15, N-4.77. Found C-73.33, H-5.13, N-4.69.

EXAMPLE 32F

5-[β-(2'-Hydroxy-3'-methoxyphenyl)ethenyl]-3-methylisoxazole

According to the procedure of Example 29, 5-isoxazoleethanol, c-[2-hydroxy-3-methoxyphenyl]-3-methyl- is reacted with HCl-methanol to afford 5-[β-(2'-hydroxy-3'-methoxyphenyl)ethenyl]-3-methylisoxazole (31%); mp=129°-131° C. Analysis for $C_{13}H_{13}NO_3$.

Calculated C-67.51, H-5.68, N-6.06. Found C-67.51, H-5.70, N-5.95.

EXAMPLE 32G

5-[β-(4'-Hydroxy-3',5'-dibromophenyl)ethenyl]-3-methylisoxazole

According to the procedure of Example 29, 5-isoxazoleethanol, α-[3,5-dibromo-4-hydroxyphenyl]-3-methyl- is reacted with HCl-methanol to afford 5-[β-(4'-hydroxy-3',5'-dibromophenyl)ethenyl]-3-methylisoxazole (15%), mp=167°–169° C. Analysis for $C_{12}H_9Br_2NO_2$. Calculated C-40.12, H-2.53, N-3.90, Br-44.49. Found C-40.18, H-2.48, N-3.64, Br-44.88.

EXAMPLE 32H

5-[β-(4'-Hydroxy-3',5'-dichlorophenyl)ethenyl]-3-methylisoxazole

A toluene (100 mL) solution of 5-isoxazoleethanol, α-[3,5-dichloro-4-hydroxyphenyl]-3-methyl- (5.5 g, 19.1 mmol) containing a catalytic amount of p-toluenesulfonic acid is warmed to reflux for 3 hours, with azeotropic removal of water. The solvent is evaporated, and the residue is chromatographed (ethyl acetate/chloroform, 1:9) to afford 5-[β-(4'-hydroxy-3',5'-dichlorophenyl)ethenyl]-3-methylisoxazole (2.3 g, 45%); mp=184°–186° C. Analysis for $C_{12}H_9Cl_2NO_2$. Calculated C-53.35, H-3.37, N-5.19. Found C-52.98, H-3.22, N-5.28.

EXAMPLE 32I

5-[β-(2'-Hydroxy-3',5'-dibromophenyl)ethenyl]-3-methylisoxazole

According to the procedure of Example 32H, 5-isoxazoleethanol, c-[2-hydroxy-3,5-dibromophenyl]-3-methyl- is reacted with p-toluenesulfonic acid/toluene to afford 5-[β-(2'-hydroxy-3',5'-dibromophenyl)ethenyl]-3-methylisoxazole in 70% yield, mp=150°–157° C. Analysis for $C_{12}H_9NO_2Br_2$. Calculated C-40.15, H-2.53, N-3.90. Found C-39.85, H-2.47, N-3.75.

EXAMPLE 32J

5-[β-(2'-Hydroxy-3',5'-dichlorophenyl)ethenyl]-3-methylisoxazole

According to the procedure of Example 32H, 5-isoxazoleethanol, α-[2-hydroxy-3,5-dichlorophenyl]-3-methyl- is reacted with p-toluenesulfonic acid/toluene to afford 5-[β-(2'-hydroxy-3',5'-dichlorophenyl)ethenyl]-3-methylisoxazole in 80% yield, mp=143°–145° C. Analysis for $C_{12}H_9NO_2Cl_2$. Calculated C-53.36, H-3.36, N-5.19, Cl-26.25. Found C-53.12, H-3.05, N-5.11, Cl-26.26.

EXAMPLE 33

4-Acetoxy-3-methoxycinnamaldehyde

Acetoxy vanillin (5.0 g, $2.6 \times 10^{-2}$M) is dissolved in dry THF (300 ml) with formyl methylenetriphenylphosphorane (78 g, $2.6 \times 10^{-2}$M) and refluxed under an atmosphere of argon for 80 hours. The reaction mixture is concentrated to dryness and chromatographed on flash silica to afford 4-acetoxy-3-methoxycinnamaldehyde (3 g, 54% yield); mp=83°–86° C.

EXAMPLE 34

4-Acetoxy-3-methoxycinnamaldehyde oxime

4-Acetoxy-3-methoxycinnamaldehyde (2.0 g, $9.1 \times 10^{-3}$M) is dissolved in methanol (100 ml) and cooled to 0° C. with an ice/water bath. Hydroxylamine hydrochloride (0.8 g, $1.2 \times 10^{-2}$M) is added with sodium acetate (0.97 g, $1.2 \times 10^{-2}$M) and stirred for one hour. The reaction mixture is concentrated to near dryness, and redissolved in ethyl acetate (150 ml). The residual organics are washed twice with water dried over sodium sulfate, filtered, evaporated to dryness, and chromatographed on flash silica using hexane:ethyl acetate 3:1 to afford 1.45 g of 4-acetoxy-3-methoxycinnamaldehyde oxime in 68% yield; mp=72°–74° C.

EXAMPLE 35

3-[β-(4'-Acetoxy-3'-methoxyphenyl)ethenyl]-5-phenylisoxazole

4-Acetoxy-3-methoxycinnamaldehyde oxime 10.6, $2.5 \times 10^{-3}$M) is dissolved in dry DMF (15 ml) at 0° C. under an atmosphere of argon. N-chlorosuccinimide (0.4 g, $3.0 \times 10^{-3}$M) is dissolved in dry DMF (10 ml) and transferred to the 4-acetoxycinnamaldehyde/DMF solution via cannula under an atmosphere of argon. The reaction is stirred at 0° C. for nearly two hours. Phenylacetylene (1.3 g, $1.3 \times 10^{-2}$M) is mixed with triethylamine (0.38 g, $3.8 \times 10^{-3}$M) and dry DMF (5 ml). This mixture is then added via syringe to the cinnamaldehyde/NCS mixture. The entire mixture is allowed to reach room temperature and is stirred overnight. The reaction mixture is redissolved in ethyl acetate (150 ml), washed first with water, then with brine. The organics are dried over sodium sulfate, filtered, and evaporated to dryness. The residue is chromatographed on flash silica using hexane:ethyl acetate 3:2 to afford 0.45 g of 3-[β-(4'-acetoxy-3'-methoxyphenyl)ethenyl]-5-phenylisoxazole in 54% yield; mp=139°–144° C.

EXAMPLE 35A

3-[β-(4'-Acetoxy-3'-methoxyphenyl)ethenyl]-5-(2'-hydroxyethyl)isoxazole

According to the procedure of Example 35, 4-acetoxy-3-methoxycinnamaldehyde oxime is reacted with N-chlorosuccinimide and 3-butyn-1-ol to afford 3-[β-(4'-acetoxy-3'-methoxyphenyl)ethenyl]-5-(2'-hydroxyethyl)isoxazole (2.0 g, 50%); mp=62°–64° C.

EXAMPLE 35B

3-[β-(4'-Acetoxy-3'-methoxyphenyl)ethenyl]-5-hydroxymethylisoxazole

According to the procedure of Example 35, 4-acetoxy-3-methoxycinnamaldehyde oxime is reacted with N-chlorosuccinimide and propargyl alcohol to afford 3-[β-(4'-acetoxy-3'-methoxyphenyl)ethenyl]-5-hydroxymethylisoxazole (2.5 g, 67%); sufficiently pure for further use.

EXAMPLE 35C

3-Phenyl-5-methylisoxazole

Benzaldehyde oxime (20.0 g, 0.165 mole) is dissolved in DMF (250 mL) and cooled to 4° C. in an ice bath. N-chlorosuccinimide (33.1 g, 0.248 mole) is added to the reaction mixture, and the mixture is stirred for one hour. Isopropenyl acetate (41.3 g, 0.41 mole) and triethyl amine (24.8 g, 0.247 mole) are added via an equal-pressure addition funnel to the solution of benzaldehyde hydroxamic chloride. The ice bath is removed and the mixture is stirred for 24 hours. The mixture is then taken up into ethyl acetate (1 L) and washed with water ($2 \times 1$ L). The organic layer is dried over sodium sulfate and evaporated to give a residue. Flash chromatography (hexane/ethyl acetate 9:1) affords 12.0 g of 3-phenyl-5-methylisoxazole a a yellow oil.

EXAMPLE 36

3-[β-(4'-Hydroxy-3'-methoxyphenyl)ethenyl]-5-phenylisoxazole

3-[β-(4'-Acetoxy-3'-methoxyphenyl)ethenyl]-5-phenylisoxazole (0.3 g, $8.9 \times 10^{-4}$M) is dissolved in MeOH (20 ml) and stirred with sodium methoxide (0.1 g, $1.8 \times 10^{-3}$M) for one hour. The reaction mixture is concentrated to dryness, redissolved in ethyl acetate (75 ml), and washed twice with water. The organics are dried over sodium sulfate, filtered, evaporated to dryness, and chromatographed on flash silica using hexane:ethyl acetate to afford 0.25 g of 3-[β-(4'-hydroxy-3'-methoxyphenyl)ethenyl]-5-phenylisoxazole in 97% yield; mp=135°–138° C. Calculated C-73.71, H-5.15, N-4.77. Found C-73.35, H-5.35, N-4.77.

EXAMPLE 36A

3-[β-(4'-Hydroxy-3'-methoxyphenyl)ethenyl]-5-(2'-hydroxyethyl)isoxazole

According to the procedure of Example 36, 3-[β-(4'-acetoxy-3'-methoxyphenyl)ethenyl]-5-(2'-hydroxyethyl)isoxazole is reacted with sodium methoxide/methanol to afford 3-[β-(4'-hydroxy-3'-methoxyphenyl)ethenyl]-5-(2'-hydroxyethyl)isoxazole (0.24 g, 93%); mp=127°–131° C. Analysis for $C_{14}H_{15}NO_4$. Calculated C-64.35, H-5.99, N-5.36. Found C-64.40, H-5.79, N-5.15.

EXAMPLE 36B

3-[β-(4'-Hydroxy-3'-methoxyphenyl)ethenyl]-5-hydroxymethylisoxazole

According to the procedure of Example 36, 3-[β-(4'-acetoxy-3'-methoxyphenyl)ethenyl]-5-hydroxymethylisoxazole is reacted with sodium methoxide/methanol to afford 3-[β-(4'-hydroxy-3'-methoxyphenyl)ethenyl]-5-hydroxymethylisoxazole (0.6 g, 79%); mp=139°–143° C. Analysis for $C_{13}H_{13}NO_4.0.4\ H_2O$. Calculated C-63.36, H-5.46, N-5.50. Found C-63.34, H-5.53, N-5.30.

EXAMPLE 37

3-[β-(4'-Acetoxy-3'-methoxyphenyl)ethenyl]-5-methylpyrazole

To a solution of 3-[β-(4'-hydroxy-3'-methoxyphenyl)ethenyl]-5-methylpyrazole (2.50 g, 10.9 mmoles) in pyridine (30 mL) is added acetic anhydride (5.54 g, 54.3 mmoles). The reaction is stirred at room temperature for 12 hr. After this time, the reaction mixture is added dropwise to vigorously stirred ice-water (500 mL). The resulting suspension is allowed to stand for 90 minutes and the crude diacetyl product (3.2 g) is collected by filtration. The crude diacetyl product is dissolved in acetone (300 mL), water (30 mL) and methanol (30 mL). Basic alumina (100 g, Woelm basic, tlc grade) is added and the reaction mixture refluxed for 4.5 hr. The alumina is filtered and rinsed with acetone (100 mL). The combined filtrate is evaporated and the residue partitioned between water and ethyl acetate. The organic layer is dried ($MgSO_4$) and concentrated to afford, after flash chromatography [chloroform:ethyl acetate 3:1], 1.71 g of pure 3-[β-(4'-acetoxy-3'-methoxyphenyl)ethenyl]-5-methylpyrazole; mp=131°–136° C.

Analysis for $C_{15}H_{16}N_2O_3$. Calculated C-66.16, H-5.92, N-10.29. Found C-66.49, H-5.92, N-10.29.

EXAMPLE 38

3-[β-(4'-Hydroxy-3',5'-bis(1,1-dimethylethyl)phenyl)ethenyl]-5-methylpyrazole

A solution of 5-[β-(4'-hydroxy-3',5'-bis(1,1-dimethylethyl)phenyl)ethenyl]-3-methylisoxazole (2.00 g, 6.4 mmoles), water (0.115 g, 6.4 mmoles) and molybdenum hexacarbonyl (1.27 g, 48 mmoles) in acetonitrile (75 mL) is refluxed for 12 hr under a nitrogen atmosphere. The reaction mixture is cooled and evaporated to dryness. The residue is dissolved in methanol (250 mL) and acidified to pH≈1 with 4N HCl. After stirring for 4 hr at room temperature, the methanol is evaporated. The resulting aqueous solution is neutralized with 1N NaOH and the organic material is extracted into ethyl acetate. The organic solution is passed through a pad of silica gel (150 g) and further eluted with chloroform (400 mL). The combined filtrate is evaporated to dryness, taken up in a minimal amount of ethyl acetate, and passed through a silica gel pad again. The resulting crude diketone (1.25 g) is then suspended in a mixture of acetic acid (100 mL) and 97% hydrazine (1.0 mL). The reaction mixture is stirred for 12 hr at room temperature. Evaporation affords a gummy residue which solidifies upon stirring in water (100 mL) for 30 minutes. The solid is purified by flash chromatography [methylenechloride/ethyl acetate 1:1] to afford 1.10 g of 3-[β-(4'-hydroxy-3',5'-bis(1,1-dimethylethyl)phenyl)ethenyl]-5-methylpyrazole; mp=218°–223° C. Analysis for $C_{20}H_{28}N_2O$. Calculated C-76.88, H-9.03, N-8.96. Found C-76.63, H-8.84, N-9.02.

EXAMPLE 38A

3-[β-(4'-Hydroxy-3',5'-bis(1-methylethyl)phenyl)ethenyl]-5-methylpyrazole

According to the procedure of Example 38, 5-[β-(4'-hydroxy-3',5'-bis(1-methylethyl)phenyl) ethenyl]-3-methylisoxazole is reacted with molybdenum hexacarbonyl to afford 3-[β-(4'-hydroxy-3',5'-bis(1,1-dimethylmethyl)phenyl)ethenyl]-5-methylpyrazole in 53% yield, mp=183°–184° C. Analysis for $C_{18}H_{24}N_2O.0.1\ H_2O$. Calculated C-75.54, H-8.52, N-9.79. Found C-75.33, H-8.72, N-9.46.

EXAMPLE 38B

3-[β-(4'-Hydroxy-3',5'-dimethoxyphenyl)ethenyl]-5-methylpyrazole

According to the procedure of Example 38, 5-[β-(4'-hydroxy-3',5'-dimethoxyphenyl)ethenyl]-3-methylisoxazole is reacted with molybdenum hexacarbonyl to afford 3-[β-(4'-hydroxy-3',5'-dimethoxyphenyl)ethenyl]-5-methylpyrazole in 56% yield, mp=153°–158° C. Analysis for $C_{14}H_{16}N_2O_3$. Calculated C-64.60, H-6.19, N-10.76. Found C-64.36, H-6.24, N-10.61.

EXAMPLE 38C

3-[β-(4'-Hydroxy-3'-methoxyphenyl)ethenyl]-5-methylpyrazole

According to the procedure of Example 38, 5-[β-(4'-hydroxy-3'-methoxyphenyl)ethenyl]-3-methylisoxazole is reacted with molybdenum hexacarbonyl to afford 3-[β-(4'-hydroxy-3'-methoxyphenyl)ethenyl]-5-methylpyrazole in 65% yield, mp=145°–147° C. Analysis for $C_{13}H_{14}N_2O_2$. Calculated C-67.81, H-6.13, N-12.17. Found C-67.62, H-6.18, N-11.93.

EXAMPLE 38D

3-[β-(2'-Hydroxy-3',5'-dibromophenyl)ethenyl]-5-methylpyrazole

According to the procedure of Example 38, 5-[β-(2'-hydroxy-3',5'-dibromophenyl)ethenyl]-3-methylisoxazole is reacted with molybdenum hexacarbonyl to afford 3-[β-(2'-hydroxy-3',5'-dibromophenyl)ethenyl]-5-methylpyrazole in 30% yield, mp =191°-200° C. Analysis for $C_{12}H_{10}N_2OBr_2$. Calculated C-40.26, H-2.82, N-7.82, Br-44.64. Found C-40.02, H-2.82, N-7.71, Br-44.35.

EXAMPLE 39

5-[β-(4'-Hydroxy-3',5'-dimethoxyphenyl)ethenyl]-3-methylisoxazole

A solution of 3-methyl-5-isoxazoleacetic acid (10.0 g, 71 mmol) [see reference R. G. Micetich, Canadian J. Chem., 48, 2006 (1970)], syringaldehyde (12.9 g, 71 mmol), piperidine (0.6 g, 7 mmol), and acetic acid (0.42 g, 7 mmol) in toluene (500 mL) is refluxed with azeotropic removal of water for 3 hours. The mixture is cooled, and the solid is collected by filtration. The solid is dissolved in pyridine (100 mL) and refluxed for 4 hours. The solvent is evaporated, and the residue purified by flash chromatography (methanol/chloroform 1:9) and recrystallization (ethyl acetate) to afford 5-[β-(4'-hydroxy-3',5'-dimethoxyphenyl)ethenyl]-3-methylisoxazole (7.73 g, 42%); mp=152°-155° C. Analysis for $C_{14}H_{15}NO_4$. Calculated C-64.36, H-5.79, N-5.36. Found C-64.16, H-5.69, N-5.28.

EXAMPLE 39A

5-[β-(3'-Methoxy-4'-hydroxy-5'-bromophenyl)ethenyl]-3-methylisoxazole

According to the procedure of Example 39, 5-bromovanillin is reacted with 3-methyl-5-isoxazoleacetic acid to afford 5-[β-(3'-methoxy-4'-hydroxy-5'-bromophenyl)ethenyl-3-methylisoxazole in 55% yield, mp=178°-180° C. Analysis for $C_{13}H_{12}NO_3Br$. Calculated C-50.33, H-3.90, N-4.54. Found C-50.35, H-3.88, N-4.44.

EXAMPLE 40

5-[α-Carbomethoxy-β-(4'-hydroxy-3',5'-dimethoxy phenyl)ethenyl]-3-methylisoxazole A solution of 3-methyl-5-isoxazoleacetic acid methyl ester (7.75 g, 50 mmol), syringaldehyde (9.1 g, 50 mmol), piperidine (0.42 g, 5 mmol), and acetic acid (0.3 g, 5 mmol) in toluene (250 mL) is refluxed for 12 hours with azeotropic removal of water. Concentration affords a residue which is taken up in ethyl acetate and adsorbed onto dry silica gel pad. The pad is washed with ethyl acetate, and the filtrate is then evaporated. Recrystallization from ethyl acetate/hexane gives 5-[α-carbomethoxy-β-(4'-hydroxy-3',5'-dimethoxyphenyl)ethenyl]-3-methylisoxazole (7.9 g, 50%), mp=130°-132° C. Analysis for $C_{16}H_{17}NO_6$. Calculated C-60.17, H-5.38, N-4.39. Found C-60.17, H-5.53, N-4.34.

EXAMPLE 41

5-[α-Carbomethoxy-β-(4'-hydroxy-3,5-dichlorophenyl) ethenyl]-3-methylisoxazole

According to the procedure of Example 40, 3-methyl-5-isoxazoleacetic acid methyl ester is reacted with 3,5-dichloro-4-hydroxybenzaldehyde to afford 5-[β-carbomethoxy-β-(4'-hydroxy-3',5'-dichlorophenyl)ethenyl]-3-methylisoxazole (37%), mp=198°-200° C. Analysis for $C_{14}H_{11}Cl_2NO_2$. Calculated C-51.24, H-3.39, N-4.27, Cl-21.61. Found C-50.99, H-3.28, N-4.37, Cl-20.88.

EXAMPLE 42

5-[α-Carbomethoxy-β-(4'-hydroxy-3',5'-bis(1-methylethyl)phenyl)ethenyl]-3-methylisoxazole According to the procedure of Example 40, 3-methyl-5-isoxazoleacetic acid methyl ester is reacted with 4-hydroxy-3,5-bis(1-methylethyl) benzaldehyde to afford 5-[β-carbomethoxy-β-(4'-hydroxy-3',5'-bis(1,1-dimethylmethyl)phenyl)ethenyl]-3-methylisoxazole (41%), mp=126°-128° C. Analysis for $C_{20}H_{25}NO_4$. Calculated C-69.94, H-7.35, N-4.08. Found C-69.88, H-7.29, N-3.72.

EXAMPLE 43

5-[α-Carbomethoxy-β-(4'-hydroxy-3',5'-dimethylphenyl)ethenyl]-3-methylisoxazole

According to the procedure of Example 40, 3-methyl-5-isoxazoleacetic acid methyl ester is reacted with 4-hydroxy-3,5-dimethylbenzaldehyde to afford 5-[α-carbomethoxy-β-(4'-hydroxy-3',5'-dimethylphenyl)ethenyl]-3-methylisoxazole (45%), mp=176°-178° C. Analysis for $C_{16}H_{17}NO_4$. Calculated C-66.88, H-5.98, N-4.88 Found C-66.46, H-6.01, N-4.85.

EXAMPLE 44

5-[α-Carbomethoxy-β-(4'-hydroxy-3',5'-dibromophenyl) ethenyl]-3-methylisoxazole

According to the procedure of Example 40, 3-methyl-5-isoxazoleacetic acid methyl ester is reacted with 4-hydroxy-3,5-dibromobenzaldehyde to afford 5-[β-carbomethoxy-β-(4'-hydroxy-3',5'-dibromophenyl)ethenyl]-3-methylisoxazole (48%), mp=164°-166° C. Analysis for $C_{14}H_{11}Br_2NO_4$. Calculated C-40.32, H-2.66, N-3.36, Br-38.32. Found C-40.34, H-2.61, N-3.30, Br-38.38.

EXAMPLE 45

5-[α-Carbomethoxy-β-(4'-hydroxy-3'-methoxyphenyl) ethenyl]-3-methylisoxazole

According to the procedure of Example 40, 3-methyl-5-isoxazoleacetic acid methyl ester is reacted with vanillin to afford 5-[c-carbomethoxy-β-(4'-hydroxy-3'-methoxyphenyl)ethenyl]-3-methylisoxazole (51%), mp=117°-119° C. Analysis for $C_{15}H_{15}NO_5$. Calculated C-60.17, H-5.38, N-4.39. Found C-60.17, H-5.53, N-4.34.

EXAMPLE 46

5-[α-Carbomethoxy-β-(4'-hydroxy-3',5'-bis(1,1-dimethylethyl)phenyl)ethenyl]-3-methylisoxazole According to the procedure of Example 40, 3-methyl-5-isoxazoleacetic acid methyl ester is reacted with 4-hydroxy-3,5-bis(1,1-dimethylethyl) benzaldehyde (with the exception of a longer reaction time of 6 days)

to afford 5-[α-carbomethoxy-β-(4'-hydroxy-3',5'-bis(1,1-dimethylethyl)phenyl) ethenyl]-3-methylisoxazole (25%), mp=131°–136° C. Analysis for $C_{20}H_{29}NO_4$. Calculated C-71.13, H-7.87, N-3.77. Found C-71.41, H-7.99, N-3.75.

EXAMPLE 46A

5-Carbomethoxy-β-(3'-methoxy-4'-hydroxy-5'-bromophenyl)ethenyl]-3-methylisoxazole According to the procedure of Example 40, 3-methyl-5-isoxazoleacetic acid methyl ester is reacted with 5-bromovanillin to afford 5-[α-carbomethoxy-β-(3'-methoxy-4'-hydroxy-5'-bromophenyl)ethenyl]-3-methylisoxazole in 38% yield, mp=138°–140° C. Analysis for $C_{15}H_{14}NO_5Br$. Calculated C-48.93, H-3.84, N-3.80, Br-21.70. Found C-49.10, H-3.88, N-3.96, Br-21.35.

EXAMPLE 47

5-[α-Carboxy-β-(4'-hydroxy-3',5'-dimethoxyphenyl) ethenyl]-3-methylisoxazole

A solution of 5-[c-carbomethoxy-β-(4'-hydroxy-3',5'-dimethoxyphenyl)ethenyl]-3-methylisoxazole (3.0 g, 9.4 mmol) in 1N aqueous KOH (100 mL) is stirred at room temperature for 18 hours. The solution is acidified with aqueous HCl and the precipitate formed is collected by filtration. Recrystallization from methanol/water 1:9 affords 5-[α-carboxy-β-(4'-hydroxy-3',5'-dimethoxyphenyl)ethenyl]-3-methylisoxazole (2.17 g, 76%); mp=217°–219° C. Analysis for $C_{15}H_{15}NO_6$. Calculated C-59.01, H-4.96, N-4.59. Found C-58.96, H-4.90, N-4.51.

EXAMPLE 48

5-[α-Carboxy-β-(4'-hydroxy-3',5'-dichlorophenyl) ethenyl]-3-methylisoxazole

According to the procedure of Example 47, 5-[α-carbomethoxy-β-(4'-hydroxy-3',5'-dichlorophenyl) ethenyl]-3-methylisoxazole is saponified to afford 5-[α-carboxy-β-(4'-hydroxy-3',5'-dichlorophenyl) ethenyl]-3-methylisoxazole (64%), mp=229°–230° C. Analysis for $C_{13}H_9Cl_2NO_4$. Calculated C-49.70, H-2.89, N-4.46, Cl-22.57. Found C-49.46, H-2.65, N-4.17, Cl-22.54.

EXAMPLE 49

5-[α-Carboxy-β-(4'-hydroxy-3',5'-bis(1-methylethyl)-phenyl)ethenyl]phenyl)ethenyl]-3-methylisoxazole According to the procedure of Example 47, 5-[α-carbomethoxy-β-(4'-hydroxy-3',5'-bis(1-methyl ethyl)-phenyl)ethenyl]-3-methylisoxazole is saponified to afford 5-[α-carboxy-β-(4'-hydroxy-3',5'-bis(1,1-dimethylmethyl)phenyl)ethenyl]-3-methylisoxazole (83%), mp=192°–194° C. Analysis for $C_{19}H_{23}NO_4$. Calculated C-69.27, H-7.05, N-4.25. Found C-69.51, H-7.06, N-4.16.

EXAMPLE 50

5-[α-Carboxy-β-(4'-hydroxy-3'-methoxyphenyl)ethenyl]-3-methylisoxazole

According to the procedure of Example 47, 5-[α-carbomethoxy-β-(4'-hydroxy-3'-methoxyphenyl) ethenyl]-3-methylisoxazole is saponified to afford 5-[α-carboxy-β-(4'-hydroxy-3'-methoxyphenyl)ethenyl]-3-methylisoxazole (73%), mp=198°–199° C. Analysis for $C_{14}H_{13}NO_5$. Calculated C-61.08, H-4.77, N-5.09. Found C-60.74, H-4.72, N-4.65.

EXAMPLE 51

5-[αCarboxy-β-(4'-hydroxy-3',5'-bis(1,1-dimethylethyl)phenyl)ethenyl]-3-methylisoxazole According to the procedure of Example 47, 5-[α-carbomethoxy-β-(4'-hydroxy-3',5'-bis(1,1-dimethylethyl)-phenyl)ethenyl]-3-methylisoxazole is saponified to afford 5-[α-carboxy-β-(4'-hydroxy-3',5'-bis(1,1-dimethylethyl)phenyl)ethenyl]-3-methylisoxazole (85%), mp=219°–221° C. Analysis for $C_{21}H_{27}NO_4$. Calculated C-70.55, H-7.63, N-3.92. Found C-70.48, H-7.64, N-3.84.

EXAMPLE 52

5-[α-Carboxy-β-(4'-hydroxy-3',5,-dimethylphenyl) ethenyl]-3-methylisoxazole

According to the procedure of Example 47, 5-[α-carbomethoxy-β-(4'-hydroxy-3',5'-dimethylphenyl)ethenyl]-3-methylisoxazole is saponified to afford 5-[α-carboxy-β-(4'-hydroxy-3',5'-dimethylphenyl)ethenyl]-3-methylisoxazole (90%), mp 228°–229° C. Analysis for $C_{15}H_{15}NO_4$. Calculated C-65.91, H-5.54, N-5.13. Found C-66.30, H-5.62, N-5.06.

EXAMPLE 53

5-[α-Carboxy-β-(4'-hydroxy-3',5'-dibromophenyl) ethenyl]-3-methylisoxazole

According to the procedure of Example 47, 5-[α-carbomethoxy-β-(4'-hydroxy-3',5'-dibromophenyl) ethenyl]-3-methylisoxazole is saponified to afford 5-[α-carboxy-β-(4'-hydroxy-3',5'-dibromophenyl) ethenyl]-3-methylisoxazole (77%), mp=229°–230° C. Analysis for $C_{13}H_9Br_2NO_4$. Calculated C-38.74, H-2.02, N-3.48, Br-39.65. Found C-38.75, H-2.20, N-3.45, Br-39.93.

EXAMPLE 53A

5-[β-Carboxy-β-(3'-methoxy-4'-hydroxy-5'-bromophenyl)ethenyl]-3-methylisoxazole

According to the procedure of Example 47, 5-[α-carbomethoxy-β-(3'-methoxy-4'-hydroxy-5'-bromophenyl)ethenyl]-3-methylisoxazole is saponified to afford 5-[α-carboxy-β-(3'-methoxy-4'-hydroxy-5'-bromophenyl)ethenyl]-3-methylisoxazole (98%), mp=225°–227° C. Analysis for $C_{14}H_{12}NO_5Br$. Calculated C-47.47, H-3.42, N-3.96, Br-22.56. Found C-47.45, H-3.42, N-4.14, Br-22.84.

EXAMPLE 54

3-[β-(4'-Hydroxy-3',5'-bis(1,1-dimethylethyl)phenyl) ethenyl]-5-methylisoxazole

According to the procedure of Example 39, 5-methyl-3-isoxazoleacetic acid is reacted with 4-hydroxy-3,5-bis(1,1-dimethylethyl)benzaldehyde to afford 3-[β-(4'-hydroxy-3',5'-bis(1,1-dimethylethyl) phenyl)ethenyl]-5-methylisoxazole in 44% yield. Mp=172°–174° C. Analysis for $C_{20}H_{27}NO_2$. Calculated C-76.64, H-8.68, N-4.47. Found C-76.44, H-8.58, N-4.59.

EXAMPLE 54A

3-[β-(4'-Hydroxy-3',5'-dibromophenyl)ethenyl]-5-methylisoxazole

According to the procedure of Example 39, 5-methyl-3-isoxazoleacetic acid is reacted with 4-hydroxy-3,5-dibromobenzaldehyde to afford 3-[β-(4'-hydroxy-3',5'-dibromophenyl)ethenyl]-5-methylisoxazole in 86% yield, mp=178°–182° C. Analysis for $C_{12}H_9NO_2Br_2$.

Calculated C-40.14, H-2.53, N-3.90. Found C-40.09, H-2.54, N-3.99.

EXAMPLE 55

3-[β-(4'-Hydroxy-3',5'-bis(1,1-dimethylethyl)phenyl) ethenyl]-5-carboxymethylisoxazole A solution of 3-[β-(4'-hydroxy-3',5'-bis(1,1-dimethylethyl)phenyl)ethenyl]-5-methylisoxazole (0.5 g, 1.6 mmol) in THF (15 mL) is cooled to −78° C. N-butyllithium (2 mL, 3.2 mmol) is added dropwise, and the solution is stirred for an additional 20 minutes. The reaction mixture is then poured onto dry ice and allowed to come to room temperature under a flow of argon gas. Water (100 mL) is added and the mixture is extracted with ethyl acetate (200 mL). The organic layer is washed with saturated aqueous $NH_4Cl$ (1×) and water (2×), then dried over sodium sulfate. Chromatography of the residue on silica (chloroform/methanol 95:5 containing 0.1% acetic acid) affords 3-[β-(4'-hydroxy-3',5'-bis(1,1-dimethylethyl)phenyl)ethenyl]-5-carboxymethylisoxazole (0.4 g, 70%), mp=205°-210° C. Analysis for $C_{21}H_{27}NO_4$. Calculated C-70.56, H-7.61, N-3.92. Found C-70.19, H-7.86, N-3.80.

EXAMPLE 56

3-[β-(4'-Hydroxy-3',5'-bis(1,1-dimethylethyl)phenyl) ethenyl]-5-methylpyrazole

A solution of 3-methyl-5-pyrazoleacetic acid (20.0 g, 0.14 mol), 4-hydroxy-3,5-bis(1,1-dimethylethyl)benzaldehyde (33.4 g, 0.14 mol), piperidine (1.2 g, 0.014 mol), and acetic acid (0.85 g, 0.014 mol) in toluene (1 L) is refluxed for 24 hours with azeotropic removal of water. The mixture is cooled and evaporated to afford a residue, which is dissolved in methanol/ethyl acetate (1:9) and extracted with water (300 mL). The organic layer is evaporated and recrystallized from hexane/ethyl acetate (5:1) to afford 3-[β-(4'-hydroxy-3',5'-bis(1,1-dimethylethyl)phenyl)ethenyl]-5-methylpyrazole (27.4 g, 61%). Mp=220°-224° C. Analysis for $C_{20}H_{28}N_2O$. Calculated C-76.88, H-9.03, N-8.96. Found C-77.15, H-9.14, N-9.09.

EXAMPLE 57

3-[β-(4'-Hydroxy-3',5'-dimethylphenyl)ethenyl]-5-methylpyrazole

According to the procedure of Example 56, 3-methyl-5-pyrazoleacetic acid is reacted with 4-hydroxy-3,5-dimethylbenzaldehyde to afford 3-[β-(4'-hydroxy-3',5'-dimethylphenyl)ethenyl]-5-methylpyrazole in 50% yield. Mp=185°-188° C. Analysis for $C_{14}H_{16}N_2O$. Calculated C-73.66, H-7.06, N-12.27. Found C-73.68, H-7.13, N-12.26.

EXAMPLE 58

3-[β-(4'-Hydroxy-3',5'-dibromophenyl)ethenyl]-5-methylpyrazole

According to the procedure of Example 56, 3-methyl-5-pyrazoleacetic acid is reacted with 4-hydroxy-3,5-dibromobenzaldehyde to afford 3-[β-(4'-hydroxy-3',5'-dibromophenyl)ethenyl]-5-methylpyrazole in 51% yield. Mp=101°-108° C. Analysis for $C_{12}H_{10}Br_2N_2O$. Calculated C-40.26, H-2.82, N-7.82. Found C-39.92, H-2.83, N-7.70.

EXAMPLE 58A

3-[β-(3'-Methoxy-4'-hydroxy-5'-bromophenyl) ethenyl]-5-methylpyrazole

According to the procedure of Example 56, 3-methyl-5-pyrazoleacetic acid is reacted with 3-methoxy-4-hydroxy-5-bromobenzaldehyde to afford 3-[β-(3'-methoxy-4'-hydroxy-5'-bromophenyl)ethenyl]-5-methylpyrazole in 20% yield; mp=158°-160° C. Analysis for $C_{13}H_{13}N_2O_2Br$. Calculated C-50.50, H-4.24, N-9.06. Found C-50.84, H-4.37, N-8.88.

EXAMPLE 59

3-[α-Carbomethoxy-β-(4'-hydroxy-3',5'-dibromophenyl) ethenyl]-5-methylpyrazole

According to the procedure of Example 40, 3-methyl-5-pyrazoleacetic acid methyl ester is reacted with 4-hydroxy-3,5-dibromobenzaldehyde to afford 3-[β-carbomethoxy-β-(4'-hydroxy-3',5'-dibromophenyl)ethenyl]-5-methylpyrazole in 40% yield, mp=182°-184° C.

EXAMPLE 59A

3-[α-Carbomethoxy-β-(4'-hydroxy-3',5'-dichlorophenyl) ethenyl-5-methylpyrazole

According to the procedure of Example 40, 3-methyl-5-isoxazoleacetic acid methyl ester is reacted with 4-hydroxy-3,5-dichlorobenzaldehyde to afford 3-[α-carbomethoxy-β-(4'-hydroxy-3',5'-dichlorophenyl)ethenyl]-5-methylpyrazole in 16% yield, mp=210°-212° C. Analysis for $C_{14}H_{12}N_2O_3Cl_2$. Calculated C-51.39, H-3.70, N-8.56. Found C-51.77, H-3.80, N-8.43.

EXAMPLE 59B

3-[α-Carbomethoxy-β-(3'-methoxy-4'-hydroxy-5'-bromophenyl)ethenyl]-5-methylpyrazole According to the procedure of Example 40, 3-methyl-5-pyrazoleacetic acid methyl ester is reacted with 5-bromovanillin to afford 3-[α-carbomethoxy-β-(3'-methoxy-4'-hydroxy-5'-bromophenyl)ethenyl]-5-methylpyrazole in 17% yield, mp=200°-201° C. Analysis for $C_{15}H_{15}N_2O_4Br$. Calculated C-49.06, H-4.13, N-7.63. Found C-49.29, H-4.11, N-7.66.

EXAMPLE 60

3-Methyl-5-pyrazoleacetic acid methyl ester

A solution of 3-methyl-5-pyrazoleacetic acid (5.0 g, 35.7 mmol) [see C. Ainsworth, *J. Amer. Chem. Soc.*, 76, 3172 (1954)] in methanol (50 mL) is saturated with HCl gas. The mixture is warmed to reflux for 5 hours, after which the solution is concentrated. The solid residue is taken up in chloroform and washed with 0.5N aqueous sodium bicarbonate, dried over $MgSO_4$, and evaporated to afford 3-methyl-5-pyrazoleacetic acid methyl ester (3.9 g, 70%) sufficiently pure for further use.

EXAMPLE 61

3-[α-Carboxy-β-(4'-hydroxy-3',5'-dibromophenyl) ethenyl]-5-methylpyrazole

According to the procedure of Example 47, 3-[α-carbomethoxy-β-(4'-hydroxy-3',5'-dibromophenyl) ethenyl]-5-methylpyrazole is saponified to afford 3-[α-carboxy-β-(4'-hydroxy-3',5'-dibromophenyl) ethenyl]-5-methylpyrazole in 88% yield, mp=194°-197° C.

Analysis for $C_{13}H_{10}N_2O_3Br_2$. Calculated C-38.83, H-2.51, N-6.97. Found C-38.80, H-2.51, N-6.98.

EXAMPLE 62

3-[α-Carboxy-β-(4'-hydroxy-3',5'-dichlorophenyl) ethenyl]-5-methylpyrazole

According to the procedure of Example 47, 3-[α-carbomethoxy-β-(4'-hydroxy-3',5'-dichlorophenyl) ethenyl]-5-methylpyrazole is saponified to afford 3-[α-carboxy-β-(4'-hydroxy-3',5'-dichlorophenyl) ethenyl]-5-methylpyrazole in 71% yield, mp=223°–225° C. Analysis for $C_{13}H_{10}N_2O_3Cl_2$. Calculated C-49.87, H-3.23, N-8.95, Cl-22.64. Found C-49.66, H-3.13, N-8.82, Cl-22.72.

EXAMPLE 63

3-[α-Carboxy-β-(3'-methoxy-4'-hydroxy-5'-bromophenyl) ethenyl]-5-methylpyrazole

According to the procedure of Example 47, 3-[α-carbomethoxy-β-(3'-methoxy-4'-hydroxy-5'-bromophenyl)ethenyl]-5-methylpyrazole is saponified to afford 3-[α-carboxy-β-(3'-methoxy-4'-hydroxy-5'-bromophenyl)ethenyl]-5-methylpyrazole in 65% yield, mp=145°–148° C. Analysis for $C_{14}H_{13}N_2O_4Br.0.5\ H_2O$. Calculated C-46.42, H-3.62, N-7.74, Br-22.06. Found C-46.64, H-3.82, N-7.82, Br-22.01.

EXAMPLE 64

5-[β-(4'-Hydroxy-3'-methoxyphenyl)ethenyl]-3-methylisothiazole

To a suspension of 4-acetoxy-3-methoxybenzyltriphenyl phosphonium chloride [L. Lonsky et al., *Manatshefte für chemie*, 107, 685–695 (1976)] (2.24 g, 4.7 mmol) in dry THF (100 mL) and DMSO (4 mL) at 0° C. under an argon atmosphere is added sodium hydride, 60% suspension in oil (0.18 g, 4.7 mmol). The reaction mixture is stirred at room temperature for one hour and then 3-methylisothiazole-5-carboxaldehyde (D. Buttimore et al., JCS, 2063, (1963)] (0.6 g, 4.7 mmol) is added. The reaction mixture is stirred at room temperature for 18 hours. The reaction mixture is poured into a saturated solution of ammonium chloride (250 mL) and the product is extracted into ethyl acetate (2×200 mL). The crude intermediate 5-[β-(4'-acetoxy-3'-methoxyphenyl) ethenyl]-3-methylisothiazole (mixture of cis and trans isomers) is purified by flash chromatography (silica, 25% EtOAc/$CH_2Cl_2$). The intermediate acetoxy compound (0.72 g).is dissolved in methanol (20 mL and treated with sodium methoxide (0.26 g) and the reaction mixture is stirred at room temperature for one hour. The reaction mixture is diluted with ethyl acetate (50 mL) and washed with water (50 mL). The organic layer is dried ($MgSO_4$) and evaporated to give 5-[β-(4'-hydroxy-3'-methoxyphenyl)ethenyl]-3-methylisothiazole (0.54 g). Flash chromatography (silica, 5% EtOAc/$CHCl_3$) gave separation of the trans and cis isomers, High $R_f$ isomer (0.35 g, 30%), $R_f$=0.53 (silica, 8:1/$CH_2Cl_2$:EtOAc); mp=187°–189° C. Low $R_f$ isomer (0.10 g, 9%), $R_f$=0.43 (silica, 8:1/$CH_2Cl_2$:EtOAc); mp=120°–124° C.

The usefulness of the compounds of the present invention as inhibitors of lipoxygenase enzyme or other related biochemical actions is demonstrated by their effectiveness in various standard test procedures. A description of each procedure follows.

5-Lipoxygenase Assay Using Isolated Human Leukocytes (5LOA₂)

The formation of 5-HETE in human leukocytes is considered a measure of 5-lipoxygenase activity. The protocol is described in the following.

Fresh heparinized or EDTA treated human blood is mixed with 6% dextran-3% dextrose in isotonic saline in the ratio 0.25 ml dextran solution per 1.0 ml blood. After mixing the blood is allowed to sit at room temperature for about 90 minutes while the RBC's settle. During this period, the plasma is removed with a plastic pipette to nalgens tubes.

The plasma is centrifuged at 800 rpm (125 kg) on the Beckman Td-b refrigerated centrifuge to remove the platelets (which remain in the supernatant). The pellet, consisting of leukocytes and erythrocytes, is treated with 10 ml 0.87% ammonium chloride at room temperature for four minutes, lysing the red cells. At the end of four minutes the cells are diluted with a 2× volume of phosphate buffered saline, pH 7.4, and centrifuged for ten minutes. The cells are washed three times with the phosphate buffered saline. Any of the pelleted cell matter which is not easily resuspended is discarded during the washings—the material contains platelets (12-lipoxygenase activity).

After washing, the cells are resuspended in phosphate buffered saline containing 1.0 mM calcium and 0.5 mM magnesium. After counting, the cells are diluted to 1.5–2.0×10⁷ leukocytes per milliliter.

To each polypropylene reaction tube is added 0.48 ml leukocytes in Ca-Mg phosphate buffered saline, pH 7.4; 1–5 μl test compound dissolved in DMSO and buffer; or DMSO for control tubes.

The tubes preincubate at 37° C. for five minutes.

The reaction is started by adding 20 μl of the ollowing, 0.5 μl, 20 mM arachidonic acid—final concentration=20 μM; 1 μl, 5 mM calcium ionophore A23187—final concentration=10 μM; and 18.5 μl buffer.

The reaction proceeds for five minutes, then is stopped by adding 0.5 ml, 0.5 mM ice-cold Tris buffer, pH 8.0. The tubes are chilled on ice for ten minutes and then extracted three times with a total of 3.5 ml ethyl acetate (3.0 ml removed).

The tubes can be stored at this point. For extended storage, the tubes should be filled with nitrogen.

The ethyl acetate is evaporated with a Sorvall Speed-Vac. The residue is dissolved in ethanol. The tubes can also be stored at this point at −20° C. under nitrogen.

A portion of the ethanol solution is injected into the HPLC system for 5-HETE quantitation.

The HPLC system consists of Hewlett-Packard 1040A UV spectrophotometry system with an HP85 computer. Injections are made automatically with a Waters WISP 710B. The pump is a Spectra Physics SP8700. Peaks are measured with a Hewlett-Packard 3390A integrator. An RP C-18 column is used. The solvent system is isocratic; the solvent is 70% methanol and 30% 0.01M sodium acetate, pH 5.7, pumped at 1.0 ml/min. The flow is monitored at 235 nm for 5-HETE quantitation. Using a 15 cm Alltech Nucleosil C-18 5 μM column provides for a sample turnaround time of about 16 minutes.

$IC_{50}$ is calculated as the amount of test agent that causes 50% inhibition of the formation of 5-HETE relative to the control.

Cyclooxygenase Enzyme Assay

Additionally, inhibition of cyclooxygenase is considered a measure of relevance to the pathophysiology of the above noted diseases. For example, see "Inhibition of Immunoglobulin E-Mediated, Antigen-Induced Monkey Asthma and Skin Reactions by 5,8,11,14-Eicosatetraynoic Acid," by Roy Patterson, M. D. and Kathleen E. Harris, B. S. in *J. Allergy Clin. Immunol.*, Vol. 67, No. 2, pp. 146–152.

The assay consists of incubating 2 mg bovine seminal vesicle powder with 2 mM epinephrine, 2.5 mM reduced glutathione, 100 μM arachidonic acid, and the test agent for 20 minutes. The reaction mixture is acidified and extracted with ethyl acetate (3 × 1.0 ml) and the pooled extract is evaporated to dryness using a Speed Vac Concentrator or under a stream of nitrogen. The residue was dissolved in ethanol. An aliquot is applied on 20×20 cm silica gel plate and developed using water:ethyl acetate:hexane:acetic acid (60:54:25:12.5, upper phase) to separate $PGE_2$ from arachidonic acid. $^{14}C$-$PGE_2$ formed is identified by co-chromatography with authentic $^{3}H$-$PGE_2$ and the amount of radioactivity is quantitated using an automatic TLC linear scanner (Berthold, Pittsburgh, Pa.) linked to an Apple II-e computer and an $IC_{50}$ is calculated as the amount of test compound causing 50% inhibition of cyclooxygenase enzyme relative to the control.

The above defined value for each of tested compounds of the present invention having the noted Example numbers are as found in the following Table 2.

TABLE 2

| Example # | 5-LO ($IC_{50}$ in μM) | BSV ($IC_{50}$ in μM) |
| --- | --- | --- |
| 1 | 1.0 | 66.0 |
| 2 | 53.0 | 67.0 |
| 3 | 15.0 | 44.0 |
| 4 | 4.3 | 40.0 |
| 5 | 7.1 | 33.0 |
| 6 | >20 | — |
| 7 | 5.5 | 34.0 |
| 8 | >20 | — |
| 9 | 7.5 | 56.0 |
| 10 | 18.0 | — |
| 12 | 29.0 | 31.0 |
| 29 | 7.8 | 10.0 |
| 30 | 6.8 | — |
| 32 | 1.8 | — |

ARBL/ARBC Whole Cell 5-Lipoxygenase and Cyclooxygenase Assays

Materials

The rat basophilic leukemia cell line (RBL-1) was obtained from the American Type Culture Collection (Rockville, Md.).

Radioimmuno assay (RIA) kits of $LTB_4$ and $PGF_{2\alpha}$ were obtained from Amersham (Arlington Heights, IL) and Seragen (Boston, Mass.) respectively.

All tissue culture media were obtained from GIBCO (Grand Island, N.Y.).

Method

RBL-1 cells were grown in culture (suspension) in Eagle's minimum essential medium supplemented with fetal bovine serum and 1:100 antibiotic-antimycotic mixture at 37° C. in an incubator supplied with air-5% carbon dioxide. Cells were harvested by centrifugation. They were washed with cold phosphate buffered saline pH 7.4 (PBS; NaCl, 7.1 g; $Na_2HPO_4$, 1.15 g; $KH_2PO_4$, 0.2 g; and KCl, 0.2 g/L). Cells were finally suspended in PBS containing 0.88 μM calcium at a density of 2.4×10$^6$ cells/ml. Cells were incubated with and without test agent (in DMSO) (1% DMSO was without effect on arachidonic acid metabolism) for ten minutes at room temperature. Calcium ionophore A23187 (5 μM) was added and cells were incubated for seven minutes at 37° C. The reaction was stopped by chilling the tubes in ice for ten minutes. Cells were separated by centrifugation and the supernatant was stored at −20°. Aliquots (100 μl) were analyzed for $LTB_4$ and $PGF_{2\alpha}$ using radioimmuno assay kits as provided by the supplier.

Table 3 contains biochemical data obtained from this RBL-1 whole cell assay.

TABLE 3

| Example # | ARBL ($IC_{50}$, μM)[a] | ARBC ($IC_{50}$, μM)[b] |
| --- | --- | --- |
| 1 | 1.6 | 2.5 |
| 5 | 0.8 | 13.0 |
| 7 | 9.5 | 6.8 |
| 10 | 5.2 | 11.0 |
| 10A | 3.8 | 4.5 |
| 10D | 0.3 | >30 |
| 10G-1 | 4.5 | >30 |
| 10G-2 | 4.1 | >30 |
| 10H | 9.5 | >30 |
| 10I | >10 | >25 |
| 10J | >10 | 30.0 |
| 10K | >20 | — |
| 10L | >20 | — |
| 10M | >30 | >30 |
| 10N | >20 | >30 |
| 10P | 12.0 | >30 |
| 10Q | >30 | >30 |
| 29 | 2.4 | 1.5 |
| 30 | 5.5 | 12.0 |
| 31 | 1.0 | 10.0 |
| 32 | 1.4 | 22.0 |
| 32B | 4.5 | 1.2 |
| 32D | <1.0 | 5.4 |
| 32E | 4.5 | 2.8 |
| 32F | 12.0 | 30.0 |
| 32G | 11.0 | 16.0 |
| 32H | 21.0 | 13.8 |
| 32J | 4.7 | >30 |
| 36 | — | — |
| 36A | 21.5 | N |
| 37 | 3.5 | — |
| 38 | 3.0 | 0.9 |
| 38A | 3.6 | 14.0 |
| 38B | 2.6 | >30 |
| 39A | 4.0 | 9.3 |
| 40 | >10 | >25 |
| 41 | >30 | 5.0 |
| 43 | 17.0 | 2.2 |
| 44 | 12.0 | 5.2 |
| 46 | 10.0 | 2.0 |
| 46A | >30 | 12.0 |
| 51 | 20.0 | 2.5 |
| 52 | >20 | >20 |
| 54 | 2.7 | ≈0.3 |
| 54B | 3.3 | 4.2 |
| 55 | 17.0 | >30 |
| 57 | 0.82 | 4.6 |
| 58 | 5.7 | 14.5 |

[a]RBL-1 intact cell 5-lipoxygenase $IC_{50}$ values (μM)
[b]RBL-1 intact cell cyclooxygenase $IC_{50}$ values (μM)

Accordingly, the present invention also includes a pharmaceutical composition for treating one of the above diseases or conditions comprising an antidisease or anticondition effective amount of a compound of the formula I as defined above together with a pharmaceutically acceptable carrier.

The present invention further includes a method for treating one of the above named diseases or conditions in mammals, including man, suffering therefrom comprising administering to such mammals either orally or parenterally, preferably oral, a corresponding pharmaceutical composition containing a compound of formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 1 to 50 mg according to the particular application and the potency of the active ingredient. The composition can, if desired, also contain other compatible therapeutic agents.

In therapeutic use as described above, the dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compoound. Thereafter the dosage is increased by small increments until the optimum effect under the circumstances is reached. For convenience, the total daily dosage may be divided and administered in portions during the day if desired.

As used herein cardiovascular diseases or conditions particularly include 1) reductions of the extent of infarct damage in a myocardial infarction, 2) prevention of recurrent myocardial infarction, 3) stroke, 4) anaphylactic shock, and 5) vasospastic disease.

An additional advantageous benefit of the cytoprotective property of the compounds of formula I are for use, for example to protect against damage from various GI tract conditions.

Various assays that are generally accepted can be used to measure cytoprotective ability.

The magnitude of a prophylactic or therapeutic dose of a compound of formula I will, of course, vary with the nature of the severity of the condition to be treated and with the particular compound of formula I and its route of administration. In general, the daily dose range for anti-asthmatic, anti-allergic or anti-inflammatory use and, generally uses other than cytoprotection, lies within the range of from about 10 $\mu$g to about 20 mg per kg body weight of a mammal, preferably from about 50 $\mu$g to about 20 mg per kg of body weight of a mammal, and most preferably from about 100 $\mu$g to about 10 mg per kg of body weight of a mammal.

The exact amount of a compound of the formula I to be used as a cytoprotective agent will depend on, inter alia, whether it is being administered to heal damaged cells or to avoid future damage, on the nature of the damaged cells (e.g., gastro-intestinal ulcerations vs.

nephrotic necrosis), and on the nature of the causative agent. An example of the use of a compound of the formula I in avoiding future damage would be co-administration of a compound of the formula I with a non-steroidal anti-inflammatory drug (for example, indomethacin) that might otherwise cause such damage. For such use, the compound of formula I is administered from 30 minutes prior up to 30 minutes after administration of the NSAID. Preferably, it is administered prior to or simultaneously with the NSAID (e.g. as a combination dosage form).

The effective daily dosage level for compounds of formula I inducing cytoprotection in mammals, especially humans, will generally range from about 0.002 mg/kg to about 100 mg/kg, preferably from about 0.02 mg/kg to about 30 mg/kg. The dosage may be administered in single or divided individual doses.

Thus, in addition to the compounds of formula I, the pharmaceutical compositions can also contain other active ingredients, such as cyclooxygenase inhibitors non-steroidal anti-inflammatory drugs (NSAIDs), peripheral analgesic agents such as zomepirac, diflunisal and the like. The weight ratio of the compound of the formula I to the second active ingredient may be varied and will depend upon the effective dose of each ingredient. Generally, an effective dose of each will be used. Thus, for example, when a compound of the formula I is combined with an NSAID, the weight ratio of the compound of the formula I to the NSAID will generally range from about 1000:1 to about 1:1000, preferably about 200:1 to about 1:200. Combinations of a compound of the formula I and other active ingredients will generally also be within the aforementioned range, but in each case, an effective dose of each active ingredient should be used.

Combinations of a compound of the formula I and other active ingredients will generally be in the aforementioned ratios. NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, pirprofen, carprofen, oxaprozin, pranoprofen, miroprofen, tioxaprofen, suprofen, alminoprofen, tiaprofen, fluprofen and bucloxic acid. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH3)COOH or —CH2CH3COOH group (which optionally can be in the form of a pharmaceutically acceptable salt group, e.g., —CH(CH3)COO−Na+ or —CH2CH2COO−Na+), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are non-narcotic analgesics/non-steroidal anti-inflammatory drugs having a free —CH2COOH group (which optionally can be in the form of a pharmaceutically acceptable salt group, e.g. —CH2COO−Na+), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

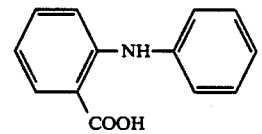

which can bear a variety of substituents and in which the free —COOH group can be in the form of a pharmaceutically acceptable salt group, e.g., —COO−Na+.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

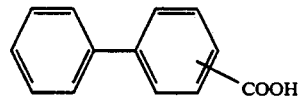

which can bear a variety of substituents and in which the free —COOH group can be in the form of a pharmaceutically acceptable salt group, e.g., —COO—Na+.

The oxicams which can be used in the present invention comprise: piroxicam, sudoxicam, isoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

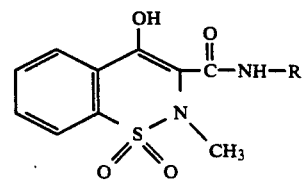

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

Finally, NSAIDs which may also be used include the salicylates, specifically aspirin, and the phenylbutazones, and pharmaceutically acceptable salts thereof.

Pharmaceutical compositions comprising the formula I compounds may also contain as the second active ingredient, antihistaminic agents such as benadryl, dramamine, histadyl, phenergan and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the formula I may also be advantageously combined with an $H_1$ or $H_2$-receptor antagonist, such as for instance cimetidine, ranitidine, terfenadine, famotidine, temelastine, acrivastine, loratadine, cetrizine, tazifylline, azelastine, aminothiadiazoles disclosed in EP 81102976.8 and like compounds, such as those disclosed in U.S. Pat. Nos. 4,283,408; 4,362,736; 4,394,508 and European Patent Application No. 40,696. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

We claim:

1. A compound of the formula (I)

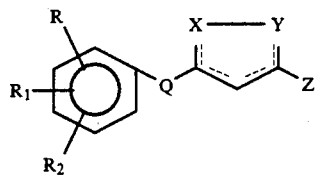

or pharmaceutically acceptable salt thereof; wherein
(1) — is a single or double bond;
(2) R, $R_1$, and $R_2$ may be the same or different and are selected from the group consisting of hydrogen, lower alkyl, hydroxy, $OR_3$ wherein $R_3$ is lower alkyl, $C(O)OR_4$ wherein $R_4$ is hydrogen or lower alkyl, $OC(O)R_3$ wherein $R_3$ is independently as defined above, $C(O)R_3$ wherein $R_3$ is independently as defined above, $NR_6R_7$ wherein $R_6$ and $R_7$ may be the same or different and are hydrogen or lower alkyl, $NHC(O)R_3$ wherein $R_3$ is independently as defined above, NHCHO, $NHSO_2R_3$ wherein $R_3$ is independently as defined above, $NHCONHR_4$ where $R_4$ is as defined above, hydroxymethyl, halogen, trifluoromethyl, $SR_4$ wherein $R_4$ is independently as defined above, or nitro;
(3) Q is CH=CH;
(4) X and Y are one of the following combinations:

| X | Y |
|---|---|
| N | $NR_5$, O or S |
| $NR_5$ | N |
| O | N |
| S | N | wherein $R_5$ is hydrogen, lower alkyl,

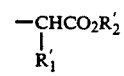

wherein $R'_1$ and $R'_2$ may be the same or different and are hydrogen or lower alkyl, $C(O)R_4$ wherein $R_4$ is independently as defined above, cycloalkyl or from three to twenty carbons having of from three to eight ring carbons optionally substituted by alkyl of from one to twelve carbons, aryl, or aralkyl;
(5) Z is aryl, aralkyl, $OC(O)R_3$ wherein $R_3$ is independently as defined above, $C(O)R_3$ wherein $R_3$ is independently as defined above, $C(O)OR_4$ wherein $R_4$ is independently as defined above, $(CH_2)_{1-2}OH$, $CH(R'_1)CO_2R'_2$ wherein $R'_1$ and $R'_2$ are independently as defined above, halogen, trifluoromethyl,

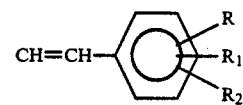

wherein R, $R_1$ and $R_2$ are independently as defined above.

2. A pharmaceutical composition for use as inhibitors of 5-lipoxygenase or cyclooxygenase comprising a 5-lipoxygenase or cyclooxygenase inhibiting amount of a compound according to claim 1, and a pharmaceutically acceptable carrier.

3. A method for treating inflammation, arthritis, ulcers, allergies, asthma, psoriasis, and cardiovascular conditions in mammals suffering therefrom comprising administering an antiinflammatory, antiallergic, antiarthritic, antiulcer, antiasthma, antipsoriatic and cardiovascular effective amount of a compound of claim 1 in unit dosage form.

4. A compound according to claim 1 wherein X and Y are N and $NR_5$ wherein $R_5$ is hydrogen.

5. A compound according to claim 1 and being 3,5-bis[β-(4'-hydroxy-3'-methoxyphenyl)ethenyl]pyrazole.

6. A compound according to claim 1 and being 3,5-bis[β-(4'-hydroxyphenyl)ethyl]pyrazole.

7. A compound which is 3-[β-(4'-hydroxy-3'-methoxyphenylethenyl]-5-trifluoromethylpyrazole.

8. A compound of the formula (I)

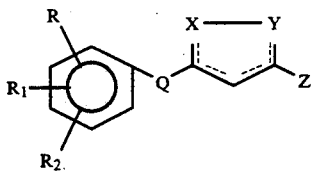

or pharmaceutically acceptable salt thereof; wherein
(1) — is a single or double bond;
(2) R, $R_1$, and $R_2$ may be the same or different and are selected from the group consisting of hydrogen, lower alkyl, hydroxy, $OR_3$ wherein $R_3$ is lower alkyl, $C(O)R_4$ wherein $R_4$ is hydrogen or lower alkyl, $OC(O)R_3$ wherein $R_3$ is independently as defined above, $C(O)R_3$ wherein $R_3$ is independently as defined above, $C(O)R_3$ wherein $R_3$ is independently as defined above, $NR_6R_7$ wherein $R_6$ and $R_7$ may be the same or different and are hydrogen or lower alkyl, $NHC(O)R_3$ wherein $R_3$ is independently as defined above, NHCHO, $NHSO_2R_3$ wherein $R_3$ is independently as defined above, $NHCONHR_4$ wherein $R_4$ is as defined above, hydroxymethyl, halogen, trifluoromethyl, $SR_4$ wherein $R_4$ is independently as defined above, or nitro;
(3) Q is CH=CH;
(4) X and Y are one of the following combinations:

| X | Y |
|---|---|
| N | O or S |
| O | N |
| S | N |

(5) Z is H, lower alkyl, aryl, aralkyl, $OC(O)R_3$ wherein $R_3$ is independently as defined above, $C(O)R_4$ wherein $R_4$ is independently as defined above, $C(O)OR_3$ wherein $R_3$ is independently as defined above, $(CH_2)_{1-2}OH$, $CH(R'_1)CO_2R'_2$ wherein $R'_1$ and $R'_2$ may be the same or different and are hydrogen or lower alkyl, halogen, trifluoromethyl,

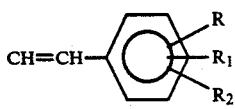

wherein R, $R_1$ and $R_2$ are independently as defined above; excluding a compound of the formula

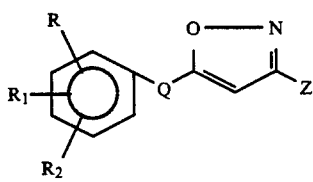

wherein one of R, $R_1$ and $R_2$ is 2-hydroxy and Z is hydrogen or alkyl.

9. A pharmaceutical composition for use as inhibitors of 5-lipoxygenase or cyclooxygenase comprising a 5-lipoxygenase or cyclooxygenase inhibiting amount of a compound according to claim 8, and a pharmaceutically acceptable carrier.

10. A method for treating inflammation, arthritis, ulcers, allergies, asthma, psoriasis, and cardiovascular conditions in mammals suffering therefrom comprising administering an antiinflammatory, antiallergic, antiarthritic, antiulcer, antiasthma, antipsoriatic and cardiovascular effective amount of a compound of claim 8 in unit dosage form.

11. A compound according to claim 8 and being 5-[β-(4'-acetoxy-3'-methoxyphenyl)ethenyl]-3-trifluoromethylisoxazole.

12. A compound according to claim 8 and being 5-[β-(4'-hydroxy-3'-methoxyphenyl)ethenyl]-3-trifluoromethylisoxazole.

13. A compound according to claim 8 and being 5-[β-(4'-hydroxy-3',5'-bis(1,1-dimethylethyl)phenyl)ethenyl]-3-methylisoxazole.

14. A compound according to claim 8 and being 5-[β-(4'-hydroxy-3'-methoxyphenyl)ethenyl]-3-methylisoxazole.

15. A compound according to claim 8 and being 5-[β-(4'-hydroxy-3',5'-bis(1-methylethyl)phenyl)ethenyl]-3-methylisoxazole.

16. A compound according to claim 8 and being 5-[β-(4'-hydroxy-3',5'-dimethoxyphenyl)ethenyl]-3-methylisoxazole.

17. A compound according to claim 8 and being 3-[β-(4'-acetoxy-3'-methoxyphenyl)ethenyl]-5-phenylisoxazole.

18. A compound according to claim 8 and being 3-[β-(4'-hydroxy-3'-methoxyphenyl)ethenyl]-5-phenylisoxazole.

19. A compound according to claim 8 and being 5-[β-(4'-hydroxy-3',5'-dimethylphenyl)ethenyl]-3-methylisoxazole.

20. A compound according to claim 8 and being 5-[β-(4'-hydroxy-3',5'-bis(1,1-dimethylethyl)phenyl)ethenyl]-3-phenylisoxazole.

21. A compound according to claim 8 and being 5-[β-(4'-hydroxy-3',5'-dimethoxyphenyl)ethenyl]-3-phenylisoxazole.

22. A compound according to claim 8 and being 5-[β-(4'-hydroxy-3'-methoxyphenyl)ethenyl]-3-phenylisoxazole.

23. A compound according to claim 8 and being 5-[β-(2'-hydroxy-3'-methoxyphenyl)ethenyl]-3-methylisoxazole.

24. A compound according to claim 8 and being 5-[β-(4'-hydroxy-3',5'-dibromophenyl)ethenyl]-3-methylisoxazole.

25. A compound according to claim 8 and being 5-[β-(4'-hydroxy-3',5'-dichlorophenyl)ethenyl]-3-methylisoxazole.

26. A compound according to claim 8 and being 5-[β-(4'-acetoxy-3'-methoxyphenyl)ethenyl]-5-(2'-hydroxyethyl)isoxazole.

27. A compound according to claim 8 and being 5-[β-(4'-acetoxy-3'-methoxyphenyl)ethenyl]-5-hydroxymethylisoxazole.

28. A compound according to claim 8 and being 3-[β-(4'-hydroxy-3'-methoxyphenyl)ethenyl]-5-(2'-hydroxyethyl)isoxazole.

29. A compound according to claim 8 and being 3-[β-(4′-hydroxy-3′-methoxyphenyl)ethenyl]-5-hydroxymethylisoxazole.

30. A compound according to claim 8 and being 3-[β-(4′-hydroxy-3′,5′-bis(1,1-dimethylethyl)phenyl)ethenyl]-5-methylisoxazole.

31. A compound according to claim 8 and being 3-[β-(4′-hydroxy-3′,5′-bis(1,1-dimethylethyl)phenyl)ethenyl]-5-carboxymethylisoxazole.

32. A compound according to claim 8 and being 5-[β-(2′-hydroxy-3′,5′-dichlorophenyl)ethenyl]-3-methylisoxazole.

33. A compound according to claim 8 and being 5-[β-(2′-hydroxy-3′,5′-dibromophenyl)ethenyl]-3-methylisoxazole.

34. A compound according to claim 8 and being 5-[β-(3′-methoxy-4′-hydroxy-5′-bromophenyl)ethenyl]-3-methylisoxazole.

35. A compound according to claim 8 and being 3-[β-(4′-hydroxy-3′,5′-dibromophenyl)ethenyl]-5-methylisoxazole.

36. A compound according to claim 8 and being (E)-5-[β-(4′-hydroxy-3′,5′-bis(1,1-dimethylethyl)phenyl)ethenyl]-3-trifluoromethylisoxazole.

37. A compound according to claim 8 and being 5-[β-(4′-hydroxy-3′-methoxyphenyl)ethenyl]-3-methylisothiazole.

38. A compound of the formula (I)

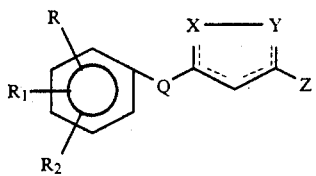   I or pharmaceutically acceptable salt thereof; wherein
(1) — is a single or double bond;
(2) R, R$_1$, and R$_2$ may be the same or different and are selected from the group consisting of hydrogen, lower alkyl, hydroxy, OR$_3$ wherein R$_3$ is lower alkyl, C(O)OR$_4$ wherein R$_4$ is hydrogen or lower alkyl, OC(O)R$_3$ wherein R$_3$ is independently as defined above, C(O)R$_3$ wherein R$_3$ is independently as defined above, NR$_6$R$_7$ wherein R$_6$ and R$_7$ may be the same or different and are hydrogen or lower alkyl, NHC(O)R$_3$ wherein R$_3$ is independently as defined above, NHCHO, NHSO$_2$R$_3$ wherein R$_3$ is independently as defined above, NHCONHR$_4$ where R$_4$ is as defined above, hydroxymethyl, halogen, trifluoromethyl, SR$_4$ wherein R$_4$ is independently as defined above, or nitro;
(3) Q is CH=CH;
(4) X and Y are one of the following combinations:

| X | Y |
|---|---|
| N | NR$_5$, O or S |
| NR$_5$ | N |
| O | N |
| S | N | wherein R$_5$ is

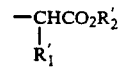

wherein R′$_1$ and R′$_2$ may be the same or different and are hydrogen or lower alkyl, C(O)R$_4$ wherein R$_4$ is independently as defined above, cycloalkyl of from three to twenty carbons having of from three to eight ring carbons optionally substituted by alkyl of from one to twelve carbons, or aralkyl;
(5) Z is H, lower alkyl, aryl, aralkyl, OC(O)R$_3$ wherein R$_3$ is independently as defined above, C(O)R$_4$ wherein R$_4$ is independently as defined above, C(O)OR$_3$ wherein R$_3$ is independently as defined above, (CH$_2$)$_{1-2}$OH, CH(R′$_1$)CO$_2$R′$_2$ wherein R′$_1$ and R′$_2$ are independently as defined above, halogen, trifluoromethyl,

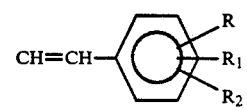

wherein R, R$_1$ and R$_2$ are independently as defined above; excluding a compound of the formula

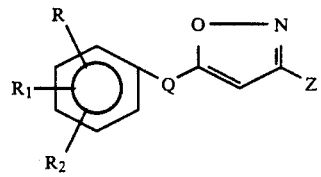

wherein one of R, R$_1$ and R$_2$ is 2-hydroxy and Z is hydrogen or alkyl.

39. A pharmaceutical composition for use as inhibitors of 5-lipoxygenase or cyclooxygenase comprising a 5-lipoxygenase or cyclooxygenase inhibiting amount of a compound according to claim 38, and a pharmaceutically acceptable carrier.

40. A method for treating inflammation, arthritis, ulcers, allergies, asthma, psoriasis, and cardiovascular conditions in mammals suffering therefrom comprising administering an antiinflammatory, antiallergic, antiarthritic, antiulcer, antiasthma, antipsoriatic and cardiovascular effective amount of a compound of claim 38 in unit dosage form.

41. A compound according to claim 38 an being ethyl-3-[β-(3-methoxy-4-hydroxyphenyl)ethenyl]-1H-pyrazole-5-carboxylate.

42. A compound according to claim 38 and being 3-[β-(3-methoxy-4-hydroxyphenyl)ethenyl]-1H-pyrazole-5-carboxylic acid.

43. A compound according to claim 38 and being (E)-5-[β-(4′-hydroxy-3′,5′-dimethoxyphenyl)ethenyl]-3-methyl-1H-pyrazole-1-acetic acid, ethyl ester.

44. A compound according to claim 38 and being 3-[β-(4-hydroxy-3′,5′-di-t-butylphenyl)ethenyl]-5-methyl-1H-pyrazole-1-acetic acid, methyl ester.

45. A compound according to claim 38 and being 5-[β-(4′-hydroxy-3′,5′-di-t-butylphenyl)ethenyl]-3-methyl-1H-pyrazole-1-acetic acid, methyl ester.

46. A compound according to claim 38 and being 3-[β-(4-hydroxy-3′,5′-dimethoxyphenyl)ethenyl]-5-methyl-1H-pyrazole-1-acetic acid, methyl ester.

47. A compound according to claim 38 and being 5-[β-(4'-hydroxy-3'-methoxyphenyl)ethenyl]-3-methyl-1H-pyrazole-1-acetic acid, methyl ester.

48. A compound according to claim 38 and being 3-[β-(4'-hydroxy-3'-methoxyphenyl)ethenyl]-5-methyl-1H-pyrazole-1-acetic acid, methyl ester.

49. A compound according to claim 38 and being 3-[β-(4'-hydroxy-3'-methoxyphenyl)ethenyl]-5-methyl-1H-pyrazole-1-acetic acid.

50. A compound according to claim 38 and being 5-[β-(4'-hydroxy-3'-methoxyphenyl)ethenyl]-3-methyl-1H-pyrazole-1-acetic acid.

51. A compound according to claim 38 and being 5-[β-(4'-hydroxy-3',5'-dimethoxyphenyl)ethenyl]-3-methyl-1H-pyrazole-1-acetic acid.

52. A compound according to claim 38 and being 3-[β-(4'-hydroxy-3',5'-dimethoxyphenyl)ethenyl]-5-methyl-1H-pyrazole-1-acetic acid.

53. A compound according to claim 38 and being 5-[β-(4'-hydroxy-3',5'-di-t-butylphenyl)ethenyl]-3-methyl-1H-pyrazole-1-acetic acid.

54. A compound according to claim 38 and being 3-[β-(4'-hydroxy-3',5'-di-t-butylphenyl)ethenyl]-5-methyl-1H-pyrazole-1-acetic acid.

55. A compound of the formula (I)

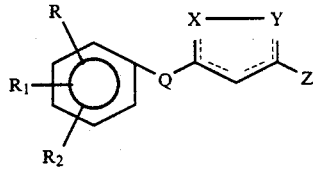

R, $R_1$, and $R_2$ may be the same or different and are selected from the group consisting of hydrogen, lower alkyl, hydroxy, $OR_3$ wherein $R_3$ is lower alkyl, $C(O)OR_4$ wherein $R_4$ is hydrogen or lower alkyl, $OC(O)R_3$ wherein $R_3$ is independently as defined above, $C(O)R_3$ wherein $R_3$ is independently as defined above, $NR_6R_7$ wherein $R_6$ and $R_7$ may be the same or different and are hydrogen or lower alkyl, $NHC(O)R_3$ wherein $R_3$ is independently as defined above, NHCHO, $NHSO_2R_3$ wherein $R_3$ is independently as defined above, $NHCONHR_4$ where $R_4$ is as defined above, hydroxymethyl, halogen, trifluoromethyl, $SR_4$ wherein $R_4$ is independently as defined above, or nitro;

(3) Q is

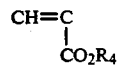

wherein $R_4$ is independently as defined above;
(4) X and Y are one of the following combinations:

| X | Y |
|---|---|
| N | $NR_5$, O or S |
| $NR_5$ | N |
| O | N |
| S | N | wherein $R_5$ is hydrogen, lower alkyl,

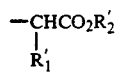

wherein $R'_1$ and $R'_2$ may be the same or different and are hydrogen or lower alkyl, $C(O)R_4$ wherein $R_4$ is independently as defined above, cycloalkyl of from three to twenty carbons having of from three to eight ring carbons optionally substituted by alkyl of from one to twelve carbons, aryl, or aralkyl;

(5) Z is H, lower alkyl, aryl, aralkyl, $OC(O)R_3$ wherein $R_3$ is independently as defined above, $C(O)R_4$ wherein $R_4$ is independently as defined above, $C(O)OR_3$ wherein $R_3$ is independently as defined above, $(CH_2)_{1-2}OH$, $CH(R'_1)CO_2R'_2$ wherein $R'_1$ and $R'_2$ are independently as defined above, halogen, trifluoromethyl,

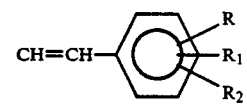

wherein R, $R_1$ and $R_2$ are independently as defined above.

56. A pharmaceutical composition for use as inhibitors of 5-lipoxygenase or cyclooxygenase comprising a 5-lipoxygenase or cyclooxygenase inhibiting amount of a compound of claim 55; and a pharmaceutically acceptable carrier.

57. A method for treating inflammation, arthritis, ulcers, allergies, asthma, psoriasis and cardiovascular conditions in mammals suffering therefrom comprising administering an antiinflammatory, antiallergic, antiarthritic, antiulcer, antiasthma, antipsoriatic and cardiovascular effective amount of a compound of claim 55 in unit dosage form.

58. A compound according to claim 55 which is 3-[α-carbomethoxy-β-(4'-hydroxy-3',5'-dibromophenyl)ethenyl]-5-methylpyrazole.

59. A compound according to claim 55 which is 3-[α-carbomethoxy-β-(4'-hydroxy-3',5'-dichlorophenyl)ethenyl]-5-methylpyrazole.

60. A compound according to claim 55 which is 3-[α-carbomethoxy-β-(3'-methoxy-4'-hydroxy-5'-bromophenyl)ethenyl]-5-methylpyrazole.

61. A compound according to claim 55 which is 3-[α-carboxy-β-(4'-hydroxy-3',5' -dibromophenyl)ethenyl]-5-methylpyrazole.

62. A compound according to claim 55 which is 3-[α-carboxy-β-(4'-hydroxy-3',5'-dichlorophenyl)ethenyl]-5-methylpyrazole.

63. A compound according to claim 55 which is 3-[α-carboxy-β-(3'-methoxy-4'-hydroxy-5'-bromophenyl)ethenyl]-5-methylpyrazole.

64. A compound according to claim 55 which is 5-[α-carbomethoxy-β-(4'-hydroxy-3',5'-dimethoxyphenyl)ethenyl]-3-methylisoxazole.

65. A compound according to claim 55 which is 5-[α-carbomethoxy-β-(4'-hydroxy-3',5'-dichlorophenyl)ethenyl]-3-methylisoxazole.

66. A compound according to claim 55 which is 5-[α-carbomethoxy-β-(4'-hydroxy-3',5'-bis(1-methylethyl)phenyl)ethenyl]-3-methylisoxazole.

67. A compound according to claim 55 which is 5-[α-carbomethoxy-β-(4'-hydroxy-3',5'-dimethylphenyl)ethenyl]-3-methylisoxazole.

68. A compound according to claim 55 which is 5-[α-carbomethoxy-β-(4'-hydroxy-3',5'-dibromophenyl)ethenyl]-3-methylisoxazole.

69. A compound according to claim 55 which is 5-[α-carbomethoxy-β-(4'-hydroxy-3'-methoxyphenyl)ethenyl]-3-methylisoxazole.

70. A compound according to claim 55 which is 5-[α-carbomethoxy-β-(4'-hydroxy-3',5'-bis(1,1-dimethylethyl)phenyl)ethenyl]-3-methylisoxazole.

71. A compound according to claim 55 which is 5-[α-carboxy-β-(4'-hydroxy-3',5'-dimethoxyphenyl)ethenyl]-3-methylisoxazole.

72. A compound according to claim 55 which is 5-[α-carboxy-β-(4'-hydroxy-3',5'-dichlorophenyl)ethenyl]-3-methylisoxazole.

73. A compound according to claim 55 which is 5-[α-carboxy-β-(4'-hydroxy-3',5'-bis(1-methylethyl)phenyl)ethenyl]-3-methylisoxazole.

74. A compound according to claim 55 which is 5-[α-carboxy-β-(4'-hydroxy-3'-methoxyphenyl)ethenyl]-3-methylisoxazole.

75. A compound according to claim 55 which is 5-[α-carboxy-β-(4'-hydroxy-3',5'-bis(1,1-dimethylethyl)phenyl)ethenyl]-3-methylisoxazole.

76. A compound according to claim 55 which is 5-[α-carboxy-β-(4'-hydroxy-3',5'-dimethylphenyl)ethenyl]-3-methylisoxazole.

77. A compound according to claim 55 which is 5-[α-carboxy-β-(4'-hydroxy-3',5'-dibromophenyl)ethenyl]-3-methylisoxazole.

78. A compound according to claim 55 which is 5-[α-carbomethoxy-β-(3'-methoxy-4'-hydroxy-5'-bromophenyl)ethenyl]-3-methylisoxazole.

79. A compound according to claim 55 which is 5-[α-carboxy-β-(3'-methoxy-4'-hydroxy-5'-bromophenyl)ethenyl]-3-methylisoxazole.

* * * * *